United States Patent
Maltz et al.

(10) Patent No.: US 11,883,687 B2
(45) Date of Patent: Jan. 30, 2024

(54) X-RAY IMAGING SYSTEM FOR RADIATION THERAPY

(71) Applicant: SHANGHAI UNITED IMAGING HEALTHCARE CO., LTD., Shanghai (CN)

(72) Inventors: Jonathan Maltz, Houston, TX (US); Johannes Stahl, Houston, TX (US); Supratik Bose, Houston, TX (US); Walter Aguilar, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 265 days.

(21) Appl. No.: 17/015,033

(22) Filed: Sep. 8, 2020

(65) Prior Publication Data

US 2020/0406064 A1    Dec. 31, 2020

(51) Int. Cl.
*A61N 5/10* (2006.01)

(52) U.S. Cl.
CPC ........... *A61N 5/1081* (2013.01); *A61N 5/103* (2013.01); *A61N 5/1049* (2013.01)

(58) Field of Classification Search
CPC ........... A61B 6/03; A61B 6/40; A61B 6/4007; A61B 6/4014; A61B 6/405; A61B 6/44; A61B 6/4429; A61B 6/4435; A61B 6/56; A61N 5/10; A61N 5/103; A61N 5/1031; A61N 5/1042; A61N 5/1048;
(Continued)

(56) References Cited

U.S. PATENT DOCUMENTS

| 2003/0048868 A1* | 3/2003 | Bailey | A61B 6/032 378/65 |
| 2006/0074304 A1* | 4/2006 | Sayeh | A61B 5/113 600/427 |

(Continued)

FOREIGN PATENT DOCUMENTS

| CN | 101628154 A | 1/2010 |
| CN | 101801272 A | 8/2010 |

(Continued)

OTHER PUBLICATIONS

International Search Report in PCT/CN2021/080638 dated Jun. 10, 2021, 5 pages.

(Continued)

*Primary Examiner* — Hoon K Song
(74) *Attorney, Agent, or Firm* — METIS IP LLC

(57) ABSTRACT

A radiation treatment system may include a gantry configured to rotate around an object, a treatment head moving with the gantry, a plurality of imaging radiation sources configured to emit imaging beams toward the object, and one or more first detectors configured to detect at least a portion of the imaging beams. When the treatment head is delivering a treatment beam to the object, the plurality of imaging radiation sources and the one or more first detectors may be positioned outside at least a portion of a maximum treatment radiation region so as not to interfere with the treatment beam. At least one of the plurality of imaging radiation sources and the one or more first detectors may be positioned at or near an edge of the maximum treatment radiation region.

20 Claims, 12 Drawing Sheets

(58) Field of Classification Search
CPC ........ A61N 5/1049; H01J 37/00; H01J 37/02; H01J 37/30; H01J 37/3002; H01J 37/302; H01J 37/304; H01J 37/3045; H01J 2237/00; H01J 2237/04; H01J 2237/045; H01J 2237/0455; H01J 2237/06; H01J 2237/083; H01J 2237/248
See application file for complete search history.

(56) References Cited

U.S. PATENT DOCUMENTS

| | | | |
|---|---|---|---|
| 2007/0003007 A1* | 1/2007 | Carrano | A61B 6/022 378/41 |
| 2007/0003021 A1 | 1/2007 | Guertin et al. | |
| 2007/0003123 A1* | 1/2007 | Fu | G06T 7/38 604/20 |
| 2007/0016014 A1* | 1/2007 | Hara | A61N 5/1049 378/65 |
| 2008/0002809 A1* | 1/2008 | Bodduluri | A61N 5/1049 378/41 |
| 2008/0205588 A1 | 8/2008 | Kim | |
| 2010/0290586 A1* | 11/2010 | Friedrich | A61B 6/4014 378/65 |
| 2013/0256551 A1* | 10/2013 | Yao | A61N 5/1082 250/393 |
| 2014/0247919 A1 | 9/2014 | Zhang et al. | |
| 2017/0106208 A1* | 4/2017 | Gauthier | A61N 5/1037 |
| 2017/0206317 A1 | 7/2017 | Ratwani et al. | |
| 2017/0273643 A1 | 9/2017 | Maurer, Jr. | |
| 2018/0192978 A1* | 7/2018 | Naylor | G02B 30/54 |
| 2019/0000406 A1 | 1/2019 | Liu et al. | |
| 2019/0168025 A1* | 6/2019 | Koponen | A61B 6/4014 |
| 2019/0175945 A1 | 6/2019 | Yan et al. | |
| 2019/0209868 A1 | 7/2019 | Stahl et al. | |
| 2019/0209869 A1 | 7/2019 | Liu et al. | |
| 2019/0336793 A1 | 11/2019 | Zhou et al. | |
| 2019/0380666 A1 | 12/2019 | Sheng et al. | |
| 2020/0167586 A1 | 5/2020 | Gao et al. | |
| 2020/0170591 A1 | 6/2020 | Gagnon et al. | |
| 2020/0303062 A1 | 9/2020 | Tao | |

FOREIGN PATENT DOCUMENTS

| | | |
|---|---|---|
| CN | 203634660 U | 6/2014 |
| CN | 104056367 A | 9/2014 |
| CN | 104117156 A | 10/2014 |
| CN | 101927065 B | 12/2014 |
| CN | 103282082 B | 2/2016 |
| CN | 107463786 A | 12/2017 |
| CN | 107982646 A | 5/2018 |
| CN | 108066899 A | 5/2018 |
| CN | 108319605 A | 7/2018 |
| CN | 108960640 A | 12/2018 |
| CN | 109545024 A | 3/2019 |
| CN | 109658303 A | 4/2019 |
| CN | 109741806 A | 5/2019 |
| CN | 110432920 A | 11/2019 |
| CN | 209630457 U | 11/2019 |
| CN | 110691551 A | 1/2020 |
| CN | 110917509 A | 3/2020 |
| CN | 111093764 A | 5/2020 |
| CN | 108245787 B | 6/2020 |
| WO | 2013029242 A1 | 3/2013 |

OTHER PUBLICATIONS

Written Opinion in PCT/CN2021/080638 dated Jun. 10, 2021, 5 pages.
Tomas Mikolov et al., Distributed Representations of Words and Phrases and their Compositionality, Advances in Neural Information Processing Systems, 2013, 9 pages.
Jacob Devlin et al., Bert: Pre-training of Deep Bidirectional Transformers for Language Understanding, arXiv:1810.04805, 2018, 14 pages.
Abhyuday N Jagannatha et al., Structured prediction models for RNN based sequence labeling in clinical text. Proceedings of the conference on empirical methods in natural language processing, 2016, 15 pages.
Philip John Gorinski et al., Named Entity Recognition for Electronic Health Records: A Comparison of Rule-based and Machine Learning Approaches, arXiv:1903.03985, 2019, 8 pages.
Matthew E. Peters et al., Deep contextualized word representations, arXiv:1802.05365, 2018, 15 pages.
Lei, Jianbo et al., A comprehensive study of named entity recognition in Chinese clinical text, Journal of the American Medical Informatics Association, 21(5): 808-814, 2014.

* cited by examiner

X-RAY IMAGING SYSTEM FOR RADIATION THERAPY

TECHNICAL FIELD

The present disclosure generally relates to medical technology, and more particularly, systems and methods for imaging system for radiation therapy.

BACKGROUND

Radiation therapy is a localized treatment for a specific target tissue (a target volume), such as a cancerous tumor. Dosimetric and geometric data are checked before, after, or during the treatment, to ensure correct patient placement and that the administered radiotherapy treatment matches the previously planned treatment. This process is referred to as image guided radiation therapy (IGRT), and involves the use of an imaging system to view target tissues while radiation treatment is delivered to the target volume.

SUMMARY

According to a first aspect of the present disclosure, a radiation treatment system may include a gantry configured to rotate around an object. The radiation treatment system may also include a treatment head moving with the gantry. The treatment head may be configured to deliver a treatment beam to the object. The treatment beam may provide a maximum treatment radiation region. The radiation treatment system may also include a plurality of imaging radiation sources configured to emit imaging beams toward the object. The radiation treatment system may also include one or more first detectors configured to detect at least a portion of the imaging beams. When the treatment head is delivering the treatment beam to the object, the plurality of imaging radiation sources and the one or more first detectors may be positioned outside at least a portion of the maximum treatment radiation region so as not to interfere with the treatment beam. At least one of the plurality of imaging radiation sources and the one or more first detectors may be positioned at or near an edge of the maximum treatment radiation region.

In some embodiments, when the treatment head is delivering the treatment beam to the object, the plurality of imaging radiation sources may be positioned on a first side of the maximum treatment radiation region, and the one or more first detectors may be positioned on a second side of the maximum treatment radiation region.

In some embodiments, the one or more first detectors and the plurality of imaging radiation sources may be alternately arranged.

In some embodiments, when the treatment head is delivering the treatment beam to the object along a first direction, at least one of the plurality of imaging radiation sources may be positioned so that the at least one of the plurality of imaging radiation sources delivers an imaging beam along a second direction. A difference between the first direction and the second direction may be less than 30 degrees.

In some embodiments, the treatment beam may provide a maximum treatment field on an isocenter plane of the treatment beam. The treatment beam may be collimated to a target-specific treatment area that is smaller than the maximum treatment field. At least one imaging radiation source may be positioned such that a projection of the at least one imaging radiation source onto the isocenter plane is within the maximum treatment field.

In some embodiments, at least one of the plurality of imaging radiation sources or the one or more first detectors may be configured to move with the gantry.

In some embodiments, the at least one of the plurality of imaging radiation sources or the one or more first detectors may be mounted on the gantry.

In some embodiments, at least a second one of the plurality of imaging radiation sources or the one or more first detectors may be configured to move independently of the gantry.

In some embodiments, the at least second one of the plurality of imaging radiation sources or the one or more first detectors may be mounted on a ring other than the gantry.

In some embodiments, a first angular projection range of the plurality of imaging radiation sources may be a portion of a full angular projection range of the radiation treatment system.

In some embodiments, the plurality of imaging radiation sources may be configured to move to cover a second angular projection range. The first angular projection range and the second angular projection range may constitute the full angular projection range of the radiation treatment system.

In some embodiments, a first imaging radiation source of the plurality of imaging radiation sources may be configured to move, along with the corresponding first detector, around a rotation axis of the gantry and independently of the gantry in a first range without collision.

In some embodiments, at least one of the treatment head, the plurality of imaging radiation sources excluding the first imaging radiation source, or the one or more first detectors excluding the corresponding first detector may be configured to move radially away from an isocenter of the radiation treatment system to allow the independent movement of the first imaging radiation source and the corresponding first detector in a second range without collision. The second range may be larger than the first range.

In some embodiments, at least one of the plurality of imaging radiation sources may be configured to oscillate in a limited angle range less than 360 degrees.

In some embodiments, at least one of the plurality of imaging radiation sources and the one or more first detectors may be configured to move along a direction perpendicular to a rotation plane of the treatment head to increase an imaging field of view (FOV) along the direction perpendicular to the rotation plane.

In some embodiments, a patient support may be configured to move along a direction perpendicular to a rotation plane of the treatment head to increase an imaging field of view (FOV) along the direction perpendicular to the rotation plane.

In some embodiments, at least one of the plurality of imaging radiation sources may be configured to tilt with respect to a central axis of the at least one of the plurality of imaging radiation sources.

In some embodiments, at least one of the plurality of imaging radiation sources may be configured to move radially toward an isocenter of the radiation treatment system.

In some embodiments, at least one of the plurality of imaging radiation sources may be configured to be moved to distal to a collimator of the radiation treatment system.

In some embodiments, the radiation treatment system may also include a second detector located opposite to the treatment head and configured to detect the treatment beam.

In some embodiments, the second detector may be configured to detect an imaging beam emitted from at least one of the plurality of imaging radiation sources.

In some embodiments, the second detector may include an electronic portal imaging device (EPID).

In some embodiments, at least one of the one or more first detectors may include a flat panel detector or a curvilinear detector.

In some embodiments, at least one first imaging radiation source of the plurality of imaging radiation sources may be located on a rotation plane of the treatment head.

In some embodiments, at least one second imaging radiation source of the plurality of imaging radiation sources may be located on a plane different from the rotation plane.

In some embodiments, at least one of the plurality of imaging radiation sources may be configured to emit an imaging beam while the treatment head is delivering the treatment beam to the object or when a delivery of the treatment beam to the object is paused.

In some embodiments, at least two of the plurality of imaging radiation sources may be configured to emit the imaging beams concurrently or alternately.

In some embodiments, each of the plurality of imaging radiation sources may correspond to one of the one or more first detectors.

In some embodiments, at least two of the plurality of imaging radiation sources may correspond to a same detector of the one or more first detectors.

In some embodiments, at least a portion of the detected imaging beams may be transformed into three-dimensional (3D) projection data to reconstruct a 3D imaging of the object.

In some embodiments, at least one of the plurality of imaging radiation sources and the corresponding first detector of the at least one imaging radiation source may be mounted on the back of the gantry.

According to another aspect of the present disclosure, an imaging system may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may cause a treatment head of a radiation treatment system to deliver, according to a treatment plan, a treatment beam to an object. The treatment beam may provide a maximum treatment radiation region. The one or more processors may cause a plurality of imaging radiation sources and one or more first detectors of the radiation treatment system to be positioned outside the maximum treatment radiation region so as not to interfere with the treatment beam. At least one of the plurality of imaging radiation sources and the one or more first detectors may be positioned at or near an edge of the maximum treatment radiation region. The one or more processors may cause the plurality of imaging radiation sources to deliver first imaging beams to the object while the treatment head is delivering the treatment beam to the object. The one or more processors may acquire a first data set generated by the one or more first detectors by detecting at least a portion of the first imaging beams. The one or more processors may generate an image of the object based on the first data set.

In some embodiments, a first angular projection range of a combination of the plurality of static imaging radiation sources may be a portion of a full angular projection range of the radiation treatment system.

In some embodiments, the one or more processors may cause the plurality of imaging radiation sources to move to cover a second angular projection range. The first angular projection range and the second angular projection range may constitute the full angular projection range of the radiation treatment system. The one or more processors may cause the plurality of imaging radiation sources to deliver second imaging beams in the second angular projection range. The one or more processors may acquire a second data set generated by the one or more first detectors by detecting at least a portion of the second imaging beams. The one or more processors may generate the image of the object based further on the second data set.

In some embodiments, the plurality of imaging radiation sources may be caused to move to cover the second angular projection range when the treatment beam is on or off.

In some embodiments, the one or more processors may adjust the treatment plan based on the image. The one or more processors may cause the treatment head to deliver, according to the adjusted treatment plan, an adjusted treatment beam to the object.

In some embodiments, the one or more processors may adjust the treatment plan based on the image. The one or more processors may cause the treatment head to pause the delivery of the treatment beam.

According to yet another aspect of the present disclosure, an imaging method may include one or more of the following operations. One or more processors may cause a treatment head of a radiation treatment system to deliver, according to a treatment plan, a treatment beam to an object. The treatment beam may provide a maximum treatment radiation region. The one or more processors may cause a plurality of imaging radiation sources and one or more first detectors of the radiation treatment system to be positioned outside the maximum treatment radiation region so as not to interfere with the treatment beam. At least one of the plurality of imaging radiation sources and the one or more first detectors may be positioned at or near an edge of the maximum treatment radiation region. The one or more processors may cause the plurality of imaging radiation sources to deliver first imaging beams to the object while the treatment head is delivering the treatment beam to the object. The one or more processors may acquire a first data set generated by the one or more first detectors by detecting at least a portion of the first imaging beams. The one or more processors may generate an image of the object based on the first data set.

According to yet another aspect of the present disclosure, an imaging system may include a treatment beam delivery module configured to cause a treatment head of a radiation treatment system to deliver, according to a treatment plan, a treatment beam to an object. The treatment beam may provide a maximum treatment radiation region. The system may also include a position adjustment module configured to cause a plurality of imaging radiation sources and one or more first detectors of the radiation treatment system to be positioned outside the maximum treatment radiation region so as not to interfere with the treatment beam. At least one of the plurality of imaging radiation sources and the one or more first detectors may be positioned at or near an edge of the maximum treatment radiation region. The system may also include an imaging beam delivery module configured to cause the plurality of imaging radiation sources to deliver first imaging beams to the object while the treatment head is delivering the treatment beam to the object. The system may also include a detection module configured to acquire a first data set generated by the one or more first detectors by detecting at least a portion of the first imaging beams. The system may also include a reconstruction module configured to generate an image of the object based on the first data set.

According to yet another aspect of the present disclosure, a non-transitory computer readable medium may comprise at least one set of instructions. The at least one set of instructions may be executed by one or more processors of a computing device. The one or more processors may cause a treatment head of a radiation treatment system to deliver, according to a treatment plan, a treatment beam to an object. The treatment beam may provide a maximum treatment radiation region. The one or more processors may cause a plurality of imaging radiation sources and one or more first detectors of the radiation treatment system to be positioned outside the maximum treatment radiation region so as not to interfere with the treatment beam. At least one of the plurality of imaging radiation sources and the one or more first detectors may be positioned at or near an edge of the maximum treatment radiation region. The one or more processors may cause the plurality of imaging radiation sources to deliver first imaging beams to the object while the treatment head is delivering the treatment beam to the object. The one or more processors may acquire a first data set generated by the one or more first detectors by detecting at least a portion of the first imaging beams. The one or more processors may generate an image of the object based on the first data set.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
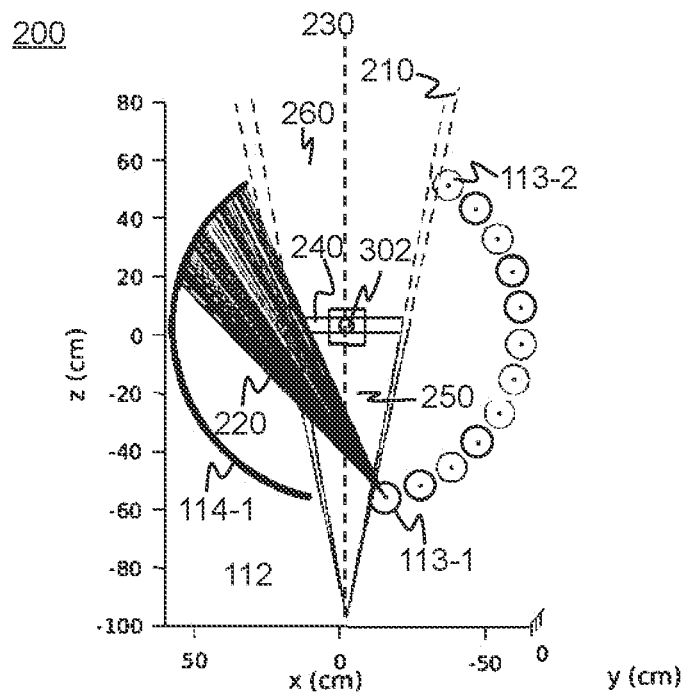
FIGS. 2 through 8 and 9A are schematic diagrams illustrating different exemplary configurations of a radiation device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding a process for exposure controlling. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

In this present disclosure, the terms "radiation therapy," "radiotherapy," "radiation treatment," and "treatment" may be used interchangeably to refer to a therapy for treating, e.g., cancers and other ailments in biological (e.g., human and animal) tissue using radiation. The terms "treatment plan," "therapy plan," and "radiotherapy plan" may be used interchangeably to refer to a plan used to perform radiotherapy.

The present disclosure provides a solution of an X-ray based intrafractional imaging of an object using a plurality of imaging radiation sources and one or more first detectors during a radiation treatment session being performed on the object. When a treatment head is delivering a treatment beam to an object, the plurality of imaging radiation sources and the one or more first detectors may be positioned outside a treatment region in which the treatment beam travels so that the plurality of imaging radiation sources and the one or more first detectors may perform imaging without obstructing the treatment beam in the treatment region. In this context, at least one of the plurality of imaging radiation sources and the one or more first detectors may be positioned at or near an edge of the treatment region.

When the treatment head is delivering the treatment beam to an object along a first direction, at least one of the plurality of imaging radiation sources may be positioned so that the at least one of the plurality of imaging radiation sources delivers an imaging beam along a second direction. A difference between the first direction and the second direction may be below 30 degrees so that the imaging beam is close to the orientation of the treatment beam. The first direction may be the direction of the center axis of the treatment beam. The second direction may be the direction of the center axis of the imaging beam of the at least one of the plurality of imaging radiation sources. In this way, more projection data related to the first direction may be acquired, thereby helping detect anatomy and/or motion of the object perpendicular to the treatment beam (e.g., the first direction). For instance, in a photon treatment, motion of tissue, an organ, or a portion thereof, in the first direction is a problematic type of motion and therefore of interest. An intrafractional imaging according to embodiments of the present disclosure in a photon treatment may be beneficial.

The system and method for X-ray based intrafractional imaging as disclosed herein provides a cost-efficient and time-efficient imaging solution to be used in IGRT and adaptive treatment. A patient or a portion thereof may be imaged during a radiation treatment session at a position where the patient is treated, thereby obviating the need to move the patient between different treatment and imaging positions and associated position adjustments with respect to a treatment plan, which in turn may save time and improve the utilization efficiency of the treatment system. Moreover, the X-ray based imaging system as disclosed herein is cheaper and/or faster than other imaging systems including, e.g., magnetic resonance imaging (MRI) system. Furthermore, an intrafractional imaging may provide timely anatomical and/or motion information for guiding the delivery of the treatment, thereby improving the accuracy of the treatment beam delivery to a target volume in the patient, reducing damages to an organ or tissue in the vicinity of the target volume due to exposure to leaked treatment radiation, and/or improving the efficacy of the treatment.

Figure 1:
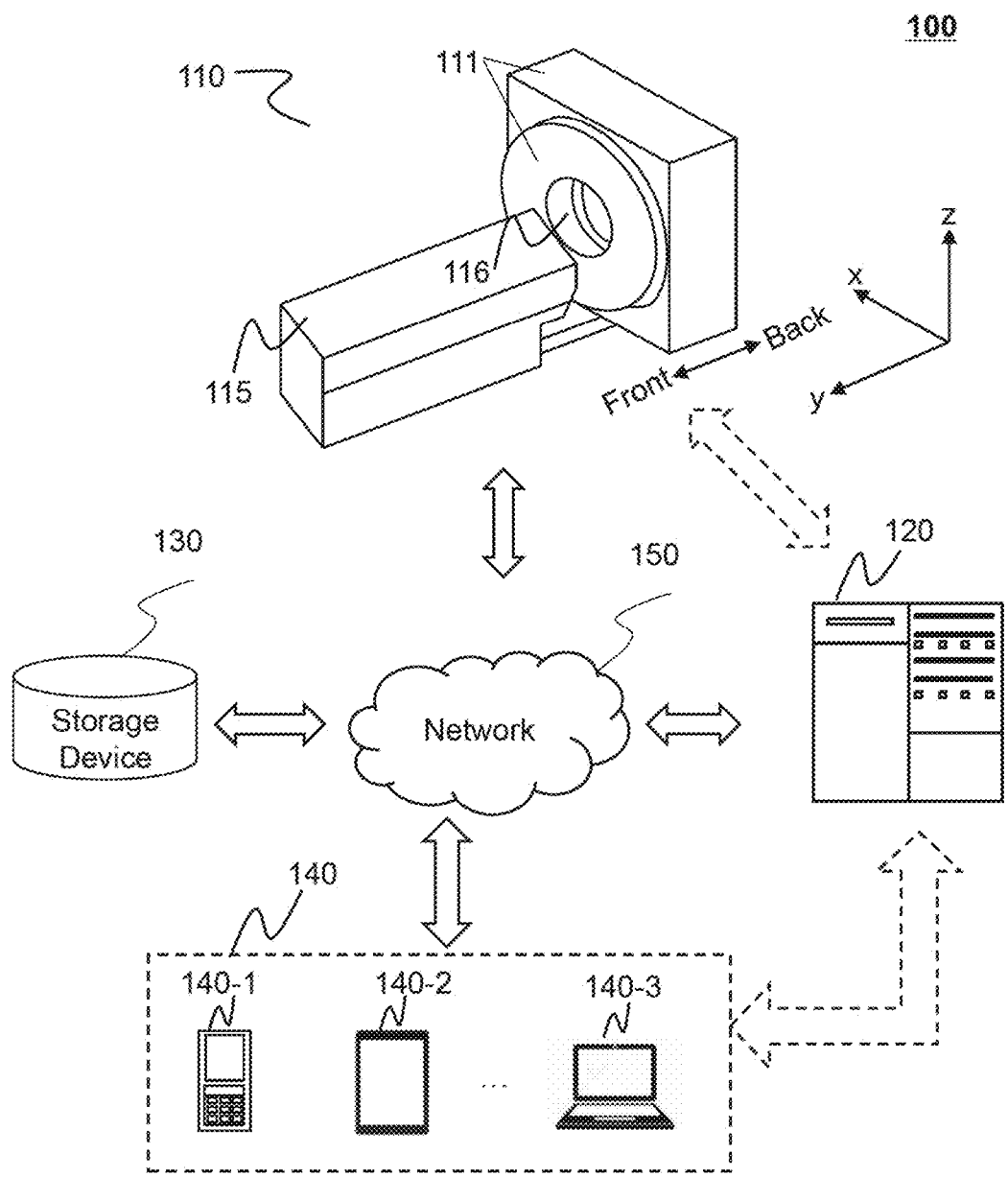
FIG. 1 is a schematic diagram illustrating an exemplary medical radiation system according to some embodiments of the present disclosure.

FIG. 1 is a schematic diagram illustrating an exemplary medical radiation system according to some embodiments of the present disclosure. In some embodiments, the medical radiation system 100 may be configured to provide radiation therapy (e.g., stereotactic radiosurgery and/or precision radiotherapy) for lesions, tumors, and conditions anywhere in a patient where radiation treatment is indicated. In some embodiments, the medical radiation system 100 may include a treatment plan system (TPS), image-guided radiotherapy (IGRT) system, etc.

As illustrated in FIG. 1, the medical radiation system 100 may include a radiation device 110, a network 150, one or more terminals 130, a processing device 120, and a storage device 130. The components in the medical radiation system 100 may be connected in one or more of various ways. Merely by way of example, the radiation device 110 may be connected to the processing device 120 through the network 150. As another example, the radiation device 110 may be connected to the processing device 120 directly as indicated by the bi-directional arrow in dotted lines linking the radiation device 110 and the processing device 120. As a further example, the storage device 130 may be connected to the processing device 120 directly or through the network 150. As still a further example, the terminal 140 may be connected to the processing device 120 directly (as indicated by the bi-directional arrow in dotted lines linking the terminal 140 and the processing device 120) or through the network 150.

In some embodiments, the medical radiation system 100 may perform image guided radiation therapy (IGRT) that monitors, using X-ray imaging, a target volume (e.g., a tumor, a lesion, etc.) to be treated inside an object (e.g., a patient). In this case, the radiation device 110 may include a treatment device (also referred to as a treatment assembly) and an imaging device (also referred to as an imaging assembly). The treatment device may be configured to deliver a treatment beam to the target volume to perform a radiotherapy on the target volume. The imaging device may be configured to perform imaging (e.g., two-dimensional (2D) imaging, three-dimensional (3D) imaging, or four-dimensional (4D) imaging) on the target volume and/or normal tissue surrounding the target volume (also referred to as "organ at risk") before, after, or while the radiotherapy is performed. In this way, the anatomy, as well as the motion or deformation, of the target volume can be detected, and the patient's position and/or the treatment beam can be adjusted for more precise radiation dose delivery to the target volume.

In some embodiments, the treatment device may include a treatment head configured to deliver a treatment beam to an object to perform a radiation treatment to a target volume inside the object. In some embodiments, the imaging device may include a plurality of imaging sources, one or more first detectors, and/or one or more second detectors. In some embodiments, the imaging device may include a computed tomography (CT) device. Details regarding the radiation device 110 can be found elsewhere in the present disclosure (e.g., descriptions in connection with FIGS. 2-7).

In the present disclosure, the x axis, the y axis, and the z axis shown in FIG. 1 may form an orthogonal coordinate system. The x axis and the y axis shown in FIG. 1 may be horizontal, and the z axis may be vertical. As illustrated, the positive x direction along the x axis may be from the right side to the left side of the radiation device 110 seen from the direction facing the front of the radiation device 110; the positive z direction along the z axis shown in FIG. 1 may be from the lower part to the upper part of the radiation device 110; the positive y direction along the y axis shown in FIG. 1 may refer to a direction in which an object is moved out of a bore of the radiation device 110.

In some embodiments, the object may be biological or non-biological. Merely by way of example, the object may include a patient, a man-made object, etc. As another example, the object may include a specific portion, organ, and/or tissue of the patient. For example, the object may include head, brain, neck, body, shoulder, arm, thorax, cardiac, stomach, blood vessel, soft tissue, knee, feet, or the like, or any combination thereof. In the present disclosure, "subject" and "object" are used interchangeably.

The network 150 may facilitate exchange of information and/or data. In some embodiments, one or more components of the medical radiation system 100 (e.g., the radiation device 110, the terminal 140, the processing device 120, or the storage device 130) may send information and/or data to another component(s) in the medical radiation system 100 via the network 150. For example, the processing device 120 may obtain a user instruction from the terminal 140 via the network 150. As another example, the processing device 120 may obtain scan data (e.g., projection data) from the radiation device 110 via the network 150. In some embodiments, the network 150 may be any type of wired or wireless network, or combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired or wireless network access points such as base stations and/or internet exchange points through which one or more components of the medical radiation system 100 may be connected to the network 150 to exchange data and/or information.

The terminal 140 include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 140 may remotely operate the radiation device 110. In some embodiments, the terminal 140 may operate the radiation device 110 via a wireless connection. In some embodiments, the terminal 140 may receive information and/or instructions inputted by a user, and send the received information and/or instructions to the radiation device 110 or to the processing device 120 via the network 150. In some embodiments, the terminal 140 may receive data and/or information from the processing device 120. In some embodiments, the terminal 140 may be part of the processing device 120. In some embodiments, the terminal 140 may be omitted.

In some embodiments, the processing device 120 may process data obtained from the radiation device 110, the terminal 140, or the storage device 130. For example, the processing device 120 may obtain projection data of an object from the radiation device 110 and generate an image of the object based on the projection data. As another example, the processing device 120 may cause one or more components (e.g., a treatment head, an imaging radiation source, a detector, a collimator, a patient support, a gantry, etc.) of the radiation device 110 to be located at a specific position. The processing device 120 may be a central processing unit (CPU), a digital signal processor (DSP), a system on a chip (SoC), a microcontroller unit (MCU), or the like, or any combination thereof.

In some embodiments, the processing device 120 may be a single server or a server group. The server group may be centralized or distributed. In some embodiments, the processing device 120 may be local or remote. For example, the processing device 120 may access information and/or data stored in the radiation device 110, the terminal 140, and/or the storage device 130 via the network 150. As another example, the processing device 120 may be directly connected to the radiation device 110, the terminal 140, and/or the storage device 130, to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data and/or instructions. In some embodiments, the storage device 130 may store data obtained from the terminal 140 and/or the processing device 120. For example, the storage device 130 may store one or more images generated by the processing device 120. In some embodiments, the storage device 130 may store data and/or instructions that the processing device 120 may execute or use to perform exemplary methods described in the present disclosure. For example, the storage device 130 may store instructions that the processing device 120 may execute or use to generate one or more images based on projection data. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more components of the medical radiation system 100 (e.g., the radiation device 110, the terminal 140, the processing device 120). One or more components of the medical radiation system 100 may access the data or instructions stored in the storage device 130 via the network 150. In some embodiments, the storage device 130 may be directly connected to or communicate with one or more components of the medical radiation system 100 (e.g., the terminal 140, the processing device 120). In some embodiments, the storage device 130 may be part of the processing device 120.

In some embodiments, the radiation device 110 may include a rotatable gantry 111 (as shown in FIG. 1), a treatment head 112 (as shown in FIGS. 2-7), a plurality of imaging radiation sources (e.g., the circles with a dot in the center in FIGS. 2 through 8 and 9A, such as 113-1 in FIG. 2, 113-2 in FIG. 7, 113-3 through 113-6 in FIGS. 4 and 5, 113-7 and 113-8 in FIGS 5, and 113-9 in FIG. 6, 113-10 through 113-12 in FIG. 8, and 113-13 in FIG. 9A), one or more first detectors (e.g., 114-1 in FIGS. 2 and 3, 114-2 and 114-3 in FIGS. 4 and 5, 114-4 in FIG. 7, 114-5 through 114-7 in FIG. 8, and 114-8 in FIG. 9A), and a patient support 115 (as shown in FIG. 1).

In some embodiments, the gantry 111 may be configured to support at least one of the treatment head 112, the plurality of imaging radiation sources, and the one or more first detectors. The gantry 111 may be configured to rotate around an object (e.g., a patient) that is moved into a field of view (FOV) (e.g., a region covered by one or more radiation beams emitted from at least one of the treatment head 112 or the plurality of imaging sources) of the radiation device 110. The gantry 111 may be rotatable around a rotation axis parallel to the y direction in FIG. 1. In some embodiments, the gantry 111 may include a C-arm gantry. For example, the treatment head 112 may be mounted on the C-arm gantry in a cantilever-like manner. In some embodiments, the gantry 111 may include a ring gantry (e.g., as shown in FIG. 1) having a toroidal shape in which the patient's body extends through a bore (e.g., the bore 116 in FIG. 1) of the ring. For example, at least one of the treatment head 112, the plurality of imaging radiation sources, and the one or more first detectors may be mounted on the perimeter of the ring gantry. In some embodiments, the gantry 111 may be configured to rotate continuously along a direction (e.g., the clockwise direction or the anticlockwise direction). In some embodiments, the gantry 111 may be configured to rotate and reverse repeatedly.

In some embodiments, the treatment head 112 may be configured to deliver a treatment beam 210 (as shown in FIGS. 2-7 and 9) to an object to perform a radiation treatment to a target volume inside the object and/or perform imaging on a region of interest (ROI) (e.g., including the target volume and/or organs at risk (OARs)) of the object. The treatment head 112 may include a linear accelerator, a cyclotron, a synchrotron, etc. The treatment head 112 may include an accelerator of species of particles including, for example, photons, electrons, protons, or heavy ions, etc. In some embodiments, the treatment beam 210 may include a relatively high energy beam (e.g., an MV beam). In some embodiments, the treatment beam 210 may include a fan beam, a cone beam, or a tetrahedron beam.

In some embodiments, the treatment head 112 may be configured to be operably coupled to or mounted on the gantry 111 and move with the gantry 111. The treatment head 112 may rotate around the rotation axis and within a rotation plane. The center point of the rotation plane may be referred to as the isocenter of the radiation device 110. The rotation axis may pass through the isocenter and be perpendicular to the rotation plane.

Figure 3:
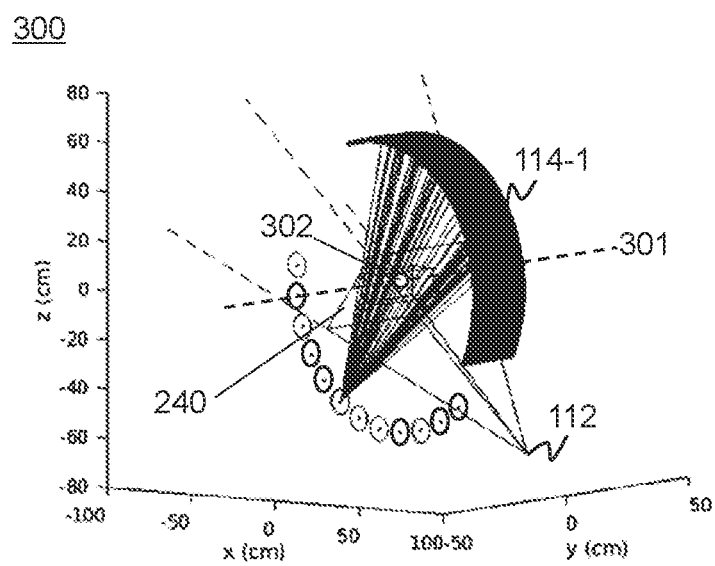

For example, as shown in FIG. 3, the radiation device 110 is located in a space whose positions are defined using a three-dimensional (3D) coordinate system as illustrated in FIG. 1. The treatment head 112 may rotate around the rotation axis 301 and within a rotation plane that is an x-z plane at y=0. The isocenter 302 (the open circle illustrated in FIGS. 2 and 3) of the radiation device 110 is located at (0, 0, 0) of the 3D coordinate system. The rotation axis 301 extends along the y direction, passes through the isocenter 302, and is perpendicular to the rotation plane.

In some embodiments, an imaging radiation source may be configured to deliver an imaging beam (e.g., beam 220 emitted from the imaging radiation source 113-1 in FIG. 2) to the object to perform imaging (e.g., 2D imaging, 3D imaging, or 4D imaging) on the ROI (e.g., including the target volume and/or the OARs) of the object. The imaging beam may include X-rays, y-rays, a-rays, ultraviolet, RF, radar, laser, neutrons, protons, or the like, or a combination thereof. In some embodiments, the imaging beam may include a relatively low energy beam (e.g., a kV beam). In some embodiments, the imaging beam may include a fan-beam, a cone beam, or a tetrahedron beam.

In some embodiments, a first detector may be configured to detect at least a portion of the imaging beams emitted from the plurality of imaging radiation sources. The first detector may include a single-row detector or a multi-row detector. The first detector may include a flat panel detector (e.g., 114-2 and 114-3 in FIGS. 4, 5, and 9) or a curvilinear detector (e.g., 114-1 in FIGS. 2 and 3, 114-8 in FIG. 9A).

In some embodiments, at least one of the plurality of imaging radiation sources or the one or more first detectors may be operably coupled to or mounted on, or separated from the gantry 111. In some embodiments, at least one of the plurality of imaging radiation sources and the one or more first detectors may move with or independently of the gantry 111. In some embodiments, at least one of the plurality of imaging radiation sources or the one or more first detectors may be operably coupled to or mounted on a ring (e.g., a slip ring 710 in FIG. 7 or a slip ring 810 in FIG. 8) other than the gantry 111. The at least one of the plurality of imaging radiation sources or the one or more first detectors may move with the slip ring. The slip ring may be operably coupled to, mounted on, or separated from the gantry 111. The slip ring may move with or independently of the gantry 111. In some embodiments, the one or more first detectors or the plurality of imaging radiation sources may be static or substantially static relative to each other.

In some embodiments, each of the plurality of imaging radiation sources may correspond to one of the one or more first detectors. In some embodiments, at least two of the plurality of imaging radiation sources may correspond to a same detector of the one or more first detectors, which indicates that the imaging beams emitted from the at least two of the plurality of imaging radiation sources are detected by the same detector of the one or more first detectors (as shown in FIGS. 2 and 3).

In some embodiments, the rotation trajectories of the treatment head 112, at least some of the plurality of imaging radiation sources and at least one of the one or more first detectors may be located along a same circle or different circles. In some embodiments, the treatment head 112, at least one of the plurality of imaging radiation sources, and at least one of the one or more first detectors may rotate in the same plane or different planes.

In some embodiments, the patient support 115 may be configured to support an object (e.g., a patient). The patient support 115 may move the object into a field of view (FOV) of the radiation device 110 along the y direction in FIG. 1.

Figure 4:
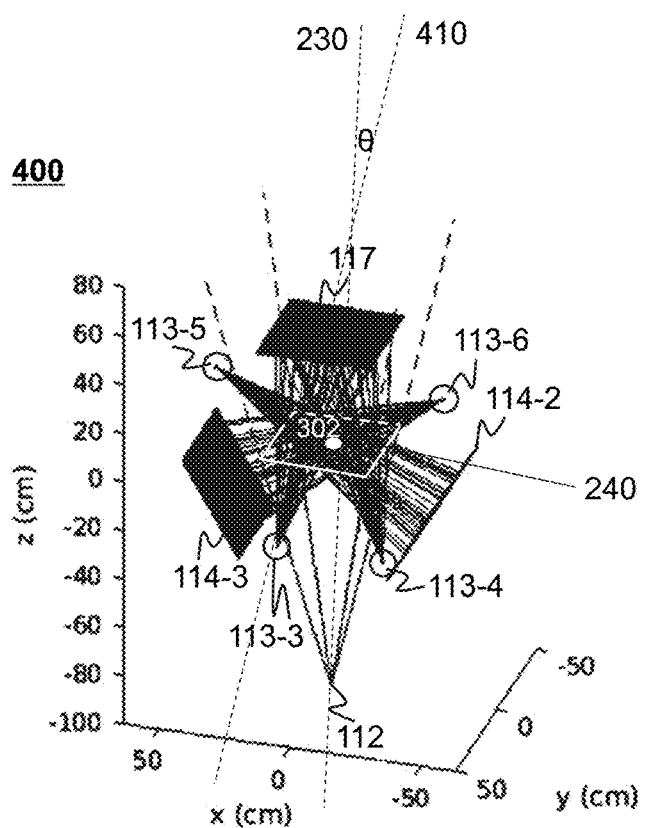
Figure 5:
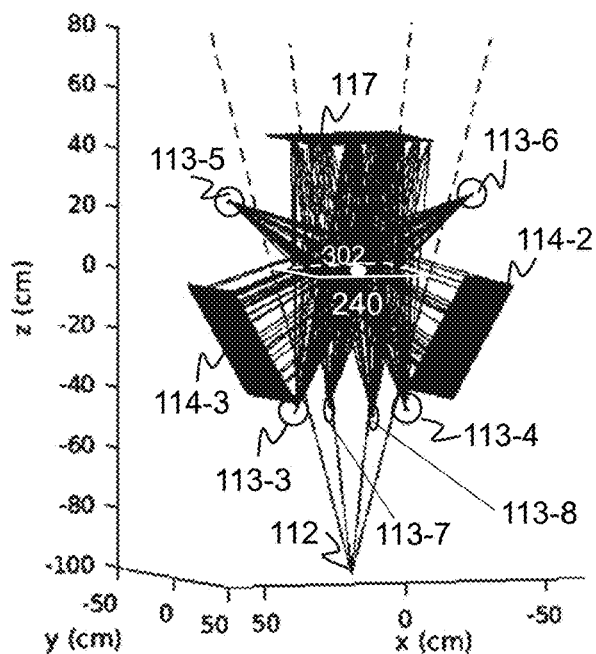

In some embodiments, the radiation device 110 may include at least one second detector 117 (as shown in FIGS. 4 5, and 9) configured to detect the treatment beam 210 emitted from the treatment head 112 and/or at least a portion of the imaging beams emitted from the plurality of imaging sources (e.g., the imaging beams emitted from the imaging radiation sources 113-3 and 113-4 in FIG. 4, or the imaging beams emitted from the imaging radiation sources 113-3, 113-4, 113-7, and 113-8 in FIG. 5). In some embodiments, the second detector 117 may include an electronic portal imaging device (EPID). In some embodiments, the second detector 117 may be operably coupled to, mounted on, or separated from the gantry 111. In some embodiments, the second detector 117 may be static. In some embodiments, the second detector 117 may move independently of the treatment head 112. In some embodiments, the second detector 117 may be positioned diametrically opposite to the treatment head 112 and rotatable with the treatment head 112. In some embodiments, the second detector may be configured to detect kV beams and also MV beams. In some embodiments, the second detector may be configured to detect kV beams only or MV beams only.

Figure 6:
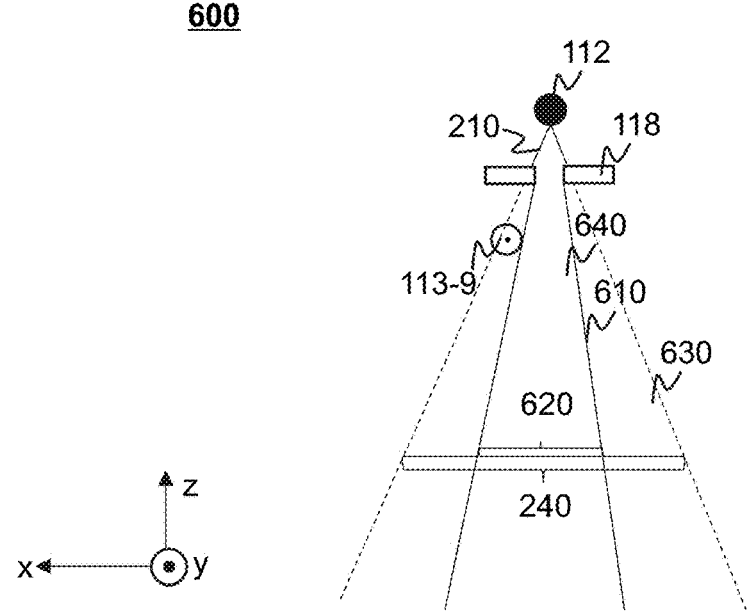

In some embodiments, the radiation device 110 may include a collimator (e.g., the collimator 118 in FIG. 6). The collimator may be positioned relative to the treatment head 112 to configure a size, location, and/or shape of the treatment beam 210 emitted from the treatment head 112 to make the collimated treatment beam approximate and target at the target volume. In some embodiments, the collimator may be positioned on a treatment beam pathway of the treatment beam 210. In some embodiments, the collimator may include a multi-leaf collimator (MLC).

In some embodiments, the treatment beam 210 may provide a maximum treatment radiation region, e.g., when there is no collimator to configure the treatment beam 210. The treatment beam 210 may travel within the maximum treatment radiation region from the treatment head 112 to the target volume.

A plane perpendicular to the central axis of the treatment beam 210 and passing through the isocenter of the radiation device 110 may be referred to as an isocenter plane. The maximum treatment radiation region may provide a maximum treatment field (e.g., 240 in FIGS. 2-7) on the isocenter plane.

The portion of the maximum treatment radiation region proximal to the isocenter plane along an emitting direction of the treatment beam 210 may be referred to as a first treatment sub-region. The portion of the maximum radiation treatment region distal to the isocenter plane along the emitting direction of the treatment beam 210 may be referred to as a second treatment sub-region.

For example, as shown in FIG. 2, the radiation device 110 is located in a space whose positions are defined using a 3D coordinate system as illustrated in FIG. 1. The isocenter 302 is located at (0, 0, 0) of the 3D coordinate system. The treatment beam 210 provides a maximum treatment field 240 on the isocenter plane perpendicular to the central axis 230 of the treatment beam 210 and passing through the isocenter 302. The first treatment sub-region 250 (the region delineated by solid lines of the treatment beam 210) and the second treatment sub-region 260 (the region delineated by the dashed lines of the treatment beam 210) may constitute the maximum treatment radiation region of the treatment beam 210.

Embodiments of the present disclosure provide a solution of using the plurality of imaging radiation sources and the one or more first detectors to perform imaging on an object while the treatment head 112 is delivering the treatment beam 210 to perform a radiation treatment on the object.

When the treatment head 112 is delivering the treatment beam 210 to an object, if there is a foreign matter (e.g., the plurality of imaging radiation sources and/or the one or more first detectors) within the first treatment sub-region, the foreign matter may obstruct at least a portion of the treatment beam 210 from reaching the object, thereby affecting the radiation treatment and/or the imaging of the object. In addition, the exposure of a device, e.g., any one of the plurality of imaging radiation sources and the one or more first detectors, to the treatment beam 210 may cause damage to the device, which in turn may reduce the lifetime of the device.

In some embodiments, when the treatment head 112 is delivering the treatment beam 210 to an object, the plurality of imaging radiation sources and the one or more first detectors may be positioned outside the first treatment sub-region so that the plurality of imaging radiation sources and the one or more first detectors may perform imaging without interfering with the treatment beam 210. In this context, at least one of the plurality of imaging radiation sources and the one or more first detectors may be positioned in a close proximity to the first treatment sub-region. For example, at least one of the plurality of imaging radiation sources and the one or more first detectors may be positioned at or near an edge of the first treatment sub-region.

When the treatment beam 210 is also used to imaging the object (e.g., the radiation device 110 includes at least one second detector 117), if there is a foreign matter within the second treatment sub-region (e.g., between the second detector 117 and the object), the foreign matter may obstruct at least a portion of the treatment beam 210 from reaching the second detector 117, thereby affecting the imaging of the object. Additionally or alternatively, the purpose of avoiding the exposure of the plurality of imaging radiation sources and the one or more first detectors under the treatment beam 210 may be considered. For instance, when the treatment head 112 is delivering the treatment beam 210 to an object, the plurality of imaging radiation sources and the one or more first detectors may be positioned outside the treatment region (not only the first treatment sub-region but also the second treatment sub-region) so that the plurality of imaging radiation sources and the one or more first detectors may perform imaging without interfering with the treatment beam 210, and/or the exposure of the plurality of imaging radiation sources and the one or more first detectors to the treatment beam 210 is avoided. In this context, at least one of the plurality of imaging radiation sources and the one or more first detectors may be positioned in a close proximity to the treatment region. For example, at least one of the plurality of imaging radiation sources and the one or more first detectors may be positioned at or near an edge of the treatment region.

In some embodiments, the treatment beam 210 may be collimated to a collimated treatment beam. The collimated treatment beam may provide a collimated treatment radiation region that is smaller than the maximum treatment radiation region of the treatment beam 210. The collimated treatment radiation beam may provide a target-specific treatment area on the isocenter plane. The target-specific treatment area may be smaller than the maximum treatment field of the maximum radiation treatment region. The intersection of the maximum treatment radiation region with the target-specific treatment area constitutes the collimated treatment radiation region. A portion of the collimated treatment radiation region proximal to the isocenter plane along an emitting direction of the treatment beam 210 may be referred to as a third treatment sub-region. A portion of the collimated treatment radiation region distal to the isocenter plane along the emitting direction of the treatment beam 210 may be referred to as a fourth treatment sub-region.

For instance, when the treatment head 112 is delivering the treatment beam 210 to an object, the plurality of imaging radiation sources and the one or more first detectors may be positioned outside the third treatment sub-region so that the plurality of imaging radiation sources and the one or more first detectors do not interfere with the collimated treatment beam. In this context, at least one of the plurality of imaging radiation sources and the one or more first detectors may be positioned in a close proximity to the third treatment sub-region. For example, at least one of the plurality of imaging radiation sources and the one or more first detectors may be positioned at an edge of the third treatment sub-region of the collimated treatment beam, other than the first treatment sub-region of the treatment beam 210, which indicates that the at least one of the plurality of imaging radiation sources and the one or more first detectors may be positioned "near" the edge of the first treatment sub-region. In this way, a projection, along the treatment beam onto the isocenter plane, of the at least one of the plurality of imaging radiation sources and the one or more first detectors may be within the maximum treatment field of the treatment head 112.

In some embodiments, if the treatment beam 210 is also used to imaging the object (e.g., the radiation device 110 includes at least one second detector 117), when the treatment head 112 is delivering the treatment beam 210 to the object, the plurality of imaging radiation sources and the one or more first detectors may be positioned outside the collimated treatment radiation region so that the plurality of imaging radiation sources and the one or more first detectors may perform imaging without interfering with the collimated treatment beam. In this context, at least one of the plurality of imaging radiation sources and the one or more first detectors may be positioned in a close proximity to the collimated treatment radiation region. For example, at least one of the plurality of imaging radiation sources and the one or more first detectors may be positioned at an edge of the collimated treatment radiation region, other than the treatment region of the treatment beam 210, which indicates that the at least one of the plurality of imaging radiation sources and the one or more first detectors may be positioned "near" the edge of the treatment region of the treatment beam 210. In this way, a projection, along the treatment beam onto the isocenter plane, of the at least one of the plurality of imaging radiation sources and the one or more first detectors may be within the maximum treatment field of the treatment head 112.

For example, FIG. 6 is a schematic diagram illustrating a cross-section of an exemplary configuration 600 of the radiation device 110 according to some embodiments of the present disclosure. The configuration 600 of the radiation device 110 shown in FIG. 6 is a view of the radiation device 110 viewed from the direction facing the front of the radiation device 110 (e.g., along the negative y direction in FIG. 1). The x, y, and z directions in FIG. 6 may correspond to those in FIG. 1. In FIG. 6, the positive y direction is vertical to the paper and points outward.

As shown in FIG. 6, the treatment head 112 emits the treatment beam 210 that provides a first treatment sub-region 630 with the maximum treatment field 240 (e.g., 40 cm×40 cm). The treatment beam 210 is collimated by the collimator 118 to a collimated treatment beam 610. The collimated treatment beam 610 provides a third treatment sub-region 640 smaller than the first treatment sub-region 630. The collimated treatment beam 610 provides a target-specific treatment area 620 (e.g., 15 cm×15 cm) that is smaller than the maximum treatment field 240.

As shown in FIG. 6, when the treatment head 112 is delivering the treatment beam 210 to an object, an imaging radiation source 113-9 is positioned at an edge of the third treatment sub-region 640, which indicates that the imaging radiation source 113-9 is positioned near an edge of the first treatment sub-region 630. A projection, along the treatment beam 210 onto the isocenter plane, of the imaging radiation source 113-9 may be within the maximum treatment field 240.

In some embodiments, when the treatment head is delivering the treatment beam 210 to an object along a first direction, at least one of the plurality of imaging radiation sources may be positioned so that the at least one of the plurality of imaging radiation sources delivers the imaging beam along a second direction (e.g., a direction along the center axis 410 of the imaging beam emitted from the imaging radiation source 113-3 shown in FIG. 4). A difference between the first direction and the second direction may be below 30 degrees so that the imaging beam is in a close vicinity to the orientation of the treatment beam 210. The first direction may be the direction of the center axis of the treatment beam 210. The second direction may be the direction of the center axis of the imaging beam of the at least one of the plurality of imaging radiation sources. In this way, more projection data substantially along or close to the first direction may be acquired, thereby facilitating the detection of anatomy and/or motion (which for photon treatments is the most problematic type of motion) of the ROI (including, e.g., the target volume, an OAR, etc.) of the object perpendicular to the treatment beam 210 (e.g., the first direction).

Figure 8:
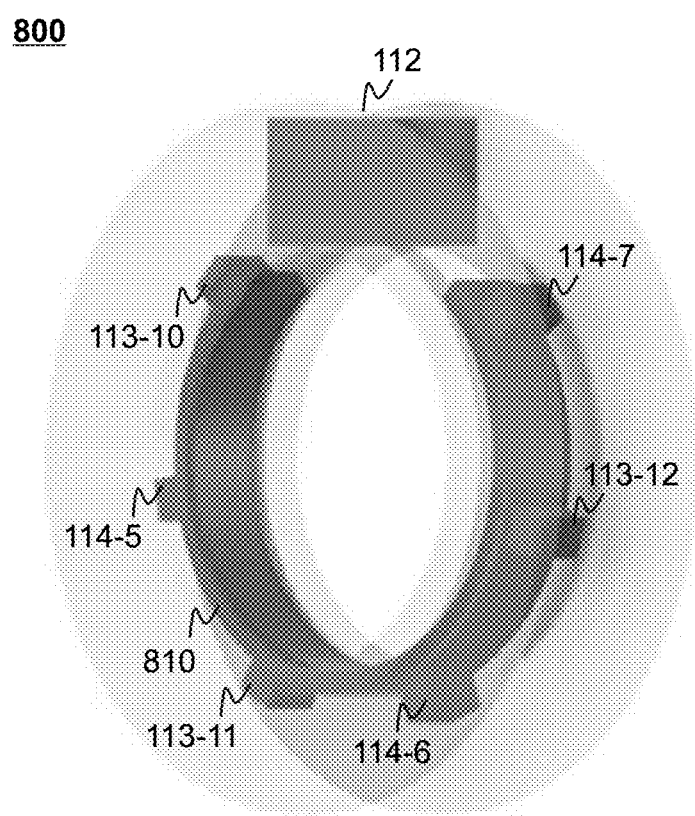

In some embodiments, the plurality of imaging radiation sources may be successively arranged and spaced apart by no first detector (as shown in FIGS. 2 and 3). In some embodiments, the one or more first detectors and the plurality of imaging radiation sources may be alternately arranged (as shown in FIGS. 4, 5, and 8). For example, at least one or two of the plurality of imaging radiation sources may be located between two first detectors. As another example, at least two first detectors may be located between two of the plurality of imaging radiation sources.

In some embodiments, at least one of the plurality of imaging radiation sources and the one or more first detectors may be positioned proximal or distal to the maximum treatment field 240 along an emitting direction of the treatment beam 210.

In some embodiments, the plurality of imaging radiation sources may be rotatable and located in the same plane or different planes. In some embodiments, at least one of the plurality of imaging radiation sources may be rotatable and located in a plane along or parallel to the rotation plane of the treatment head 112. In some embodiments, at least one of the plurality of imaging radiation sources may be rotatable and located on a plane that is perpendicular to the rotation plane of the treatment head 112.

For example, as shown in FIG. 4, the radiation device 110 is located in a space whose positions are defined using a 3D coordinate system as illustrated in FIG. 1. The isocenter 302 (represented by a white circle in FIG. 4) is located at (0, 0, 0) of the 3D coordinate system. The imaging radiation sources 113-3 through 113-6 are located on the rotation plane of the treatment head 112. The rotation plane is an x-z plane at y=0.

As another example, as shown in FIG. 5, the imaging radiation sources 113-3 through 113-6 are located on the rotation plane of the treatment head 112. The rotation plane is an x-z plane at y=0. The imaging radiation sources 113-7 and 113-8 are located on a plane perpendicular to the rotation plane of the treatment head 112. The plane is a y-z plane at x=0.

In some embodiments, at least two of the plurality of imaging radiation sources may be configured to emit the imaging beams concurrently or alternately. In some embodiments, at least one of the plurality of imaging radiation sources may be configured to emit the imaging beam while the treatment head 112 is delivering the treatment beam 210 to the object or when a delivery of the treatment beam 210 to the object is paused.

In some embodiments, a first angular projection range of a combination of the plurality of static imaging radiation sources may be a portion of a full angular projection range of the radiation treatment system. At least one of the plurality of imaging radiation sources may be configured to rotate, while the treatment head 112 is delivering the treatment beam 210 to the object or when a delivery of the treatment beam 210 to the object is paused, to cover a second angular projection range. The first angular projection range and the second angular projection range may constitute the full angular projection range of the radiation device 110.

For example, projection data of the object may be acquired for at least 180 degrees plus the imaging beam cone angle to provide full mathematical support for image reconstruction. As used herein, the at least 180 degrees plus the imaging beam cone angle may be referred to as a full angular projection range. Assuming that the imaging beam cone angle of each of the plurality of imaging radiation sources is 40 degrees, a full angular projection range is thus 220 degrees. If a first angular projection range of a combination of the plurality of static imaging radiation sources is 132 degrees, at least one of the plurality of imaging radiation sources may rotate to cover a second angular projection range of 88 degrees so that the full angular projection range of 220 degrees is covered.

In some embodiments, a first imaging radiation source (e.g., the imaging radiation source 113-13 in FIG. 9A) of the plurality of imaging radiation sources and the corresponding first detector (e.g., the first detector 114-8 in FIG. 9A) may be configured to move in a range of 360 degrees without collision with other components (e.g., the treatment head 112, the other imaging radiation sources, and the other first detectors) of the radiation device 110.

In some embodiments, a rotation radius of the first imaging radiation source and the corresponding first detector and a rotation radius of at least one of the treatment head 112, the plurality of imaging radiation sources excluding the first imaging radiation source, or the one or more first detectors excluding the corresponding first detector may be set differently such that they move in different rotation rings (e.g., rings 270-1 and 270-2 in FIG. 9) without interfering each other. As used herein, a rotation radius may refer to a radius of a rotation ring. Therefore, the first imaging radiation source and the corresponding first detector may move in the range of 360 degrees along the corresponding rotation ring without collision.

In some embodiments, a first imaging radiation source of the plurality of imaging radiation sources and the corresponding first detector may be configured to move in a limited angle range less than 360 degrees. At least one of the of the treatment head 112, the plurality of imaging radiation sources excluding the first imaging radiation source, or the one or more first detectors excluding the corresponding first detector may be configured to move radially away from an isocenter of the radiation treatment system (e.g., along a direction as indicated by arrow A in FIG. 9A) to allow movement of the first imaging radiation source and the corresponding first detector in a range of 360 degrees.

For example, the plurality of imaging radiation sources and the one or more first detectors may be positioned to move along a same rotation ring. The first imaging radiation source and the corresponding first detector may be able to move independently in a limited angle range less than 360 degrees. By the radial movement, the plurality of imaging radiation sources excluding the first imaging radiation source and the one or more first detectors excluding the corresponding first detector may make room for independent movement of the first imaging radiation source and the corresponding first detector.

In some embodiments, a first imaging radiation source of the plurality of imaging radiation sources may be configured to move, along with the corresponding first detector, around a rotation axis of the gantry and independently of the gantry in a first range less than or equal to 360 degrees without collision. In some embodiments, at least one of the treatment head, the plurality of imaging radiation sources excluding the first imaging radiation source, or the one or more first detectors excluding the corresponding first detector may be configured to move (e.g., move radially away from an isocenter of the radiation treatment system, or move along the y direction) to make room for the independent movement of the first imaging radiation source and the corresponding first detector, thereby allowing the independent movement of the first imaging radiation source and the corresponding first detector in a second range without collision. The second range may be larger than the first range.

In some embodiments at least one of the plurality of imaging radiation sources may be configured to perform a one-directional rotation (e.g., a clockwise rotation or an anti-clockwise rotation) in a range of 360 degrees. In some embodiments, at least one of the plurality of imaging radiation sources may be configured to perform an oscillation in a range of 360 degrees or a limited angle range less than 360 degrees. As used herein, an oscillation refers to moving forward and backward, e.g., along the clockwise direction and then the anti-clockwise direction, or vice versa.

Figure 7:
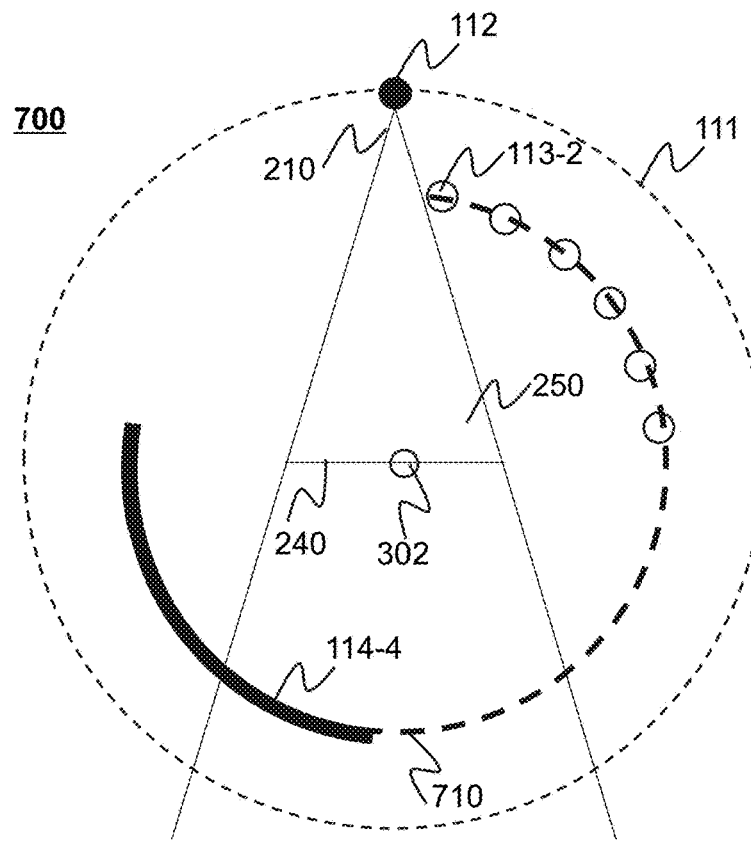

For example, FIG. 7 is a schematic diagram illustrating a cross-section of an exemplary configuration 700 of the radiation device 110 according to some embodiments of the present disclosure. The configuration 700 of the radiation device 110 shown in FIG. 7 is a view of the radiation device 110 viewed from the direction facing the front of the radiation device 110 (e.g., along the negative y direction in FIG. 1). The x, y, and z directions in FIG. 7 may correspond to those in FIG. 6.

As shown in FIG. 7, according to the configuration 700, the radiation device 110 includes a treatment head 112 mounted on a gantry 111, 6 imaging radiation sources mounted on a slip ring 710, and a first detector 114-4 that is a curvilinear detector mounted on a slip ring 710. The 6 imaging radiation sources and the first detector 114-4 are rotatable independently of the gantry 111. The slip ring 710 includes an opening. The 6 imaging radiation sources and the first detector 114-4 are configured to oscillate so as not to interfere with the first treatment sub-region 250 of the treatment beam 210 with the maximum treatment field 240. For example, when the treatment beam 210 is on, the ring carrying the 6 imaging radiation sources and the first detector 114-4 is positioned such that the 6 imaging radiation sources and the first detector 114-4 are positioned outside the first treatment sub-region 250 (e.g., as shown in FIG. 7, the imaging radiation source 113-2 is positioned at the edge of the first treatment sub-region 250); when the treatment beam 210 is off, the ring carrying the 6 imaging radiation sources and the first detector 114-4 moves anti-clockwise such that at least the imaging radiation source 113-2 is positioned in the first treatment sub-region 250 and at least a portion of the first detector 114-4 is positioned outside the first treatment sub-region 250; when the treatment beam 210 is resumed, the ring carrying the 6 imaging radiation sources and the first detector 114-4 may move clockwise such that the 6 imaging radiation sources and the first detector 114-4 are positioned outside the first treatment sub-region 250 again. By the oscillation movement, at least one of the 6 imaging radiation sources in FIG. 7 and a least a portion of the first detector 114-4 are moved into and out of the first treatment sub-region 250.

In some embodiments, at least one of the plurality of imaging radiation sources or the one or more first detectors may be configured to move along a direction (e.g., they direction in FIGS. 1-7) perpendicular to the rotation plane of the treatment head 112 to increase an imaging FOV of the plurality of imaging radiation sources along the direction perpendicular to the rotation plane (e.g., y direction in FIG. 1). In some embodiments, the patient support 115 may be configured to move along the direction perpendicular to the rotation plane of the treatment head 112 to increase the imaging FOV along the direction perpendicular to the rotation plane (e.g., y direction in FIG. 1). In some embodiments, at least one of the plurality of imaging radiation sources may be configured to tilt with respect to an axis of the at least one of the plurality of imaging radiation sources to adjust the direction of the imaging beam (e.g., the direction of the central axis of the imaging beam). Details regarding tilt with respect to an axis of the at least one of the plurality of imaging radiation sources can be found elsewhere in the present disclosure (e.g., descriptions in connection with FIG. 9B). In some embodiments, at least one of the plurality of imaging radiation sources may be configured to move radially toward the isocenter of the radiation device 110. In some embodiments, at least one of the plurality of imaging radiation sources may be configured to be moved to distal to the collimator of the radiation device 110 and positioned on a treatment beam pathway along an emitting direction of the treatment beam 210.

FIGS. 2 and 3 are schematic diagrams illustrating an exemplary configuration 200 of the radiation device 110 according to some embodiments of the present disclosure. The configuration 200 of the radiation device 110 shown in FIG. 2 is a view of the radiation device 110 viewed from the direction facing the front of the radiation device 110 (e.g., along the negative y direction in FIG. 1). FIG. 3 is a schematic diagram illustrating a 3D view of the configuration 200 of the radiation device 110. As shown in FIGS. 2 and 3, the radiation device 110 is located in a space whose positions are defined using a 3D coordinate system as illustrated in FIG. 1.

According to the configuration 200, the radiation device 110 includes a treatment head 112, 12 imaging radiation sources, and a first detector 114-1 that is a curvilinear detector. The isocenter 302 of the radiation device 110 is located at (0, 0, 0) of the 3D coordinate system. The treatment head 112 rotates around a rotation axis 301 that is parallel to the y direction and passes through the isocenter 302. The treatment head 112 rotates in a rotation plane that is an x-z plane at y=0. The treatment head 112 are configured to emit the treatment beam 210. The treatment beam 210 provides the maximum treatment field 240 on the isocenter plane that passes through the isocenter 302 and is perpendicular to the central axis 230 of the treatment beam 210.

According to the configuration 200, the 12 imaging radiation sources are successively arranged. The first detector 114-1 is located opposite to the 12 imaging radiation sources and configured to detect the imaging beams emitted from the 12 imaging radiation sources. The 12 imaging radiation sources are located and rotatable at the same plane, e.g., a plane along or parallel to the rotation plane of the treatment head 112 that is the x-z plane at y=0. The first detector 114-1 and the 12 imaging radiation sources are static or substantially static relative to each other.

When the treatment head 112 is delivering the treatment beam 210 to an object, the 12 imaging radiation sources and the first detector 114-1 are positioned without interfering with the treatment beam 210 (e.g., the first treatment sub-region 250). The 12 imaging radiation sources are positioned on a first side of the treatment beam 210, and the first detector 114-1 is positioned on a second side of the treatment beam 210. The imaging radiation source 113-1 and/or the end of the first detector 114-1 closer to the treatment head 112 is positioned at an edge of the first treatment sub-region 250.

The source-isocenter (SI) distance between the treatment head 112 and the isocenter 302 is 100 cm. The size of the maximum treatment field 240 is 40 cm×40 cm. The imaging beam cone angle of each of the 12 imaging radiation sources is 40 degrees. A full angular projection range of 220 degrees is thus required. A first angular projection range of a combination of the 12 static imaging radiation sources is 132 degrees. When the treatment head 112 is delivering the treatment beam 210 to an object, the 12 static imaging radiation sources may emit imaging beams to acquire first projection data corresponding to the first angular projection range of 132 degrees. At least one of the 12 imaging radiation sources may rotate and emit an imaging beam to acquire second projection data corresponding to a second angular projection range of 88 degrees. The first projection data and the second projection data may be used to perform 3D imaging on the object.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 4 is a schematic diagram illustrating an exemplary configuration 400 of the radiation device 110 according to some embodiments of the present disclosure. The configuration 400 of the radiation device 110 shown in FIG. 4 is a 3D view of the configuration 400 of the radiation device 110. As shown in FIG. 4, the radiation device 110 is located in a space whose positions are defined using a 3D coordinate system as illustrated in FIG. 1. The isocenter of the radiation device 110 is located at (0, 0, 0) of the 3D coordinate system.

According to the configuration 400, the radiation device 110 includes a treatment head 112, 4 imaging radiation sources 113-3 through 113-6, two first detectors 114-2 and 114-3 that are flat panel detectors, a second detector 117 that is a flat panel detector.

According to the configuration 400, the 4 imaging radiation sources 113-3 through 113-6 and the 2 first detectors 114-2 and 114-3 are alternatively arranged. The first detector 114-2 is located opposite to the imaging radiation source 113-5 and configured to detect the imaging beam emitted from the 113-5. The first detector 114-3 is located opposite to the imaging radiation source 113-6 and configured to detect the imaging beam emitted from the 113-6. The second detector 117 is configured to detect the treatment beam 210 and the imaging beams emitted from the imaging radiation sources 113-3 and 113-4. The 4 imaging radiation sources 113-3 through 113-6 are located and rotatable in the same plane, e.g., a plane along or parallel to the rotation plane of the treatment head 112 that is the x-z plane at y=0. The first detectors 114-2 and 114-3 and the 4 imaging radiation sources 113-3 through 113-6 are static or substantially static relative to each other. As used herein, two devices, e.g., two imaging radiation sources, an imaging radiation source and a detector (e.g., a first detector, a second detector) being static to each other indicates that the relative positioning of the two devices stay unchanged regardless of whether at least one of the two devices moves with respect to the gantry 111 or the patient support 115.

When the treatment head 112 is delivering the treatment beam 210 to an object, the 4 imaging radiation sources 113-3 through 113-6 and the first detectors 114-2 and 114-3 are positioned without interfering with the treatment region of the treatment beam 210. The imaging radiation sources 113-3 and 113-4, and the first detectors 114-2 and 114-3 are positioned on proximal of the maximum treatment field 240 (represented by a white parallelogram in FIG. 4) along an emitting direction of the treatment beam 210, and the imaging radiation sources 113-5 and 113-6 are positioned on distal of the maximum treatment field 240 along the emitting direction of the treatment beam 210. The imaging radiation sources 113-3 through 113-6, and the first detectors 114-2 and 114-3 are positioned at an edge of the treatment region of the treatment beam 210.

When the treatment head 112 is delivering the treatment beam 210 to an object along a first direction (e.g., the direction of the central axis 230 of the treatment beam 210 in FIG. 4), the imaging radiation sources 113-3 and 113-4 are positioned so that the imaging radiation sources 113-3 and 113-4 deliver the imaging beams along a third direction and a fourth direction, respectively. A difference between the first direction and the third direction and a different between the first direction and the fourth direction may be below 30 degrees so that the imaging beams emitted from the imaging radiation sources 113-3 and 113-4 are close to the orientation of the treatment beam 210. The third direction and the fourth direction are the directions of the central axes of the imaging radiation sources 113-3 and 113-4, respectively. For example, as shown in FIG. 4, when the treatment head 112 is delivering the treatment beam 210 to an object in or substantially in the first direction along the central axis 230, the imaging radiation sources 113-3 is positioned so as to emit an imaging beam in or substantially in the third direction 410. A difference 0 between the first direction 230 and the third direction 410 may be less than 30 degrees.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 5 is a schematic diagram illustrating an exemplary configuration 500 of the radiation device 110 according to some embodiments of the present disclosure. On the basis of the configuration 400 in FIG. 4, the radiation device 110 further includes two imaging radiation sources 113-7 and 113-8. The imaging radiation sources 113-7 and 113-8 is rotatable and located in the y-z plane at x=0. The imaging beams emitted from the imaging radiation sources 113-7 and 113-8 are detected by the second detector 117. When the treatment head 112 is delivering the treatment beam 210 to an object, the imaging radiation sources 113-7 and 113-8 are positioned at an edge of the treatment region of the treatment beam 210.

When the treatment head 112 is delivering the treatment beam 210 to an object along a first direction, the imaging radiation sources 113-7 and 113-8 are positioned so that the imaging radiation sources 113-7 and 113-8 deliver the imaging beams along a fifth direction and a sixth direction, respectively. A difference between the first direction and the fifth direction and a different between the first direction and the sixth direction may be below 30 degrees so that the imaging beams emitted from the imaging radiation sources 113-7 and 113-8 are close to the orientation of the treatment beam 210. The fifth direction and the sixth direction are the directions of the central axes of the imaging radiation sources 113-7 and 113-8, respectively.

According to the configurations 400 and 500 of the radiation device 110, more projection data related to the first direction may be acquired, thereby helping detect motion (which for photon treatments is the most problematic type of motion) of the object perpendicular to the treatment beam 210 (e.g., the first direction). Another advantage of the configurations 400 and 500 is that fewer imaging radiation sources may be used to achieve a larger angular projection range. For example, similar to the 12 imaging radiation sources in the configuration 200 in FIG. 2, the imaging beam cone angle of each of the imaging radiation sources 113-3 through 113-6 in FIG. 4 is 40 degrees. An angular projection range of a combination of the static imaging radiation sources 113-3 through 113-6 is 160 degrees larger than the angular projection range 132 degrees of a combination of the 12 static imaging radiation sources, since the imaging radiation sources 113-3 through 113-6 are sufficiently spaced.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 8 is a schematic diagram illustrating an exemplary configuration 800 of the radiation device 110 according to some embodiments of the present disclosure. The configuration 800 of the radiation device 110 shown in FIG. 8 is a 3D view of the configuration 800 of the radiation device 110.

According to the configuration 800, the radiation device 110 includes 3 imaging radiation sources 113-10 through 113-12, 3 first detectors 114-5 through 114-7. As shown in FIG. 8, the imaging radiation sources 113-10 through 113-12 and the first detectors 114-5 through 114-7 are alternatively arranged. The first detector 114-5 is configured to detect the imaging beam emitted from the imaging radiation source 113-12. The first detector 114-6 is configured to detect the imaging beam emitted from the imaging radiation source 113-10. The first detector 114-7 is configured to detect the imaging beam emitted from the imaging radiation source 113-11. The imaging radiation sources 113-10 through 113-12 and the first detectors 114-5 through 114-7 are mounted on a slip ring 810 other than a gantry of the radiation device 110. The slip ring 810 carries the imaging radiation sources 113-10 through 113-12 and the first detectors 114-5 through 114-7 to move independently of the gantry. The slip ring 810 carrying the imaging radiation sources 113-10 through 113-12 and the first detectors 114-5 through 114-7 is configured to perform a one-directional rotation (e.g., a clockwise rotation or an anti-clockwise rotation) in a range of 360 degrees, or perform an oscillation in a range of 360 degrees or a limited angle range less than 360 degrees. An oscillation refers to moving and reversing repeatedly along the clockwise direction and the anti-clockwise direction.

Figure 9A:
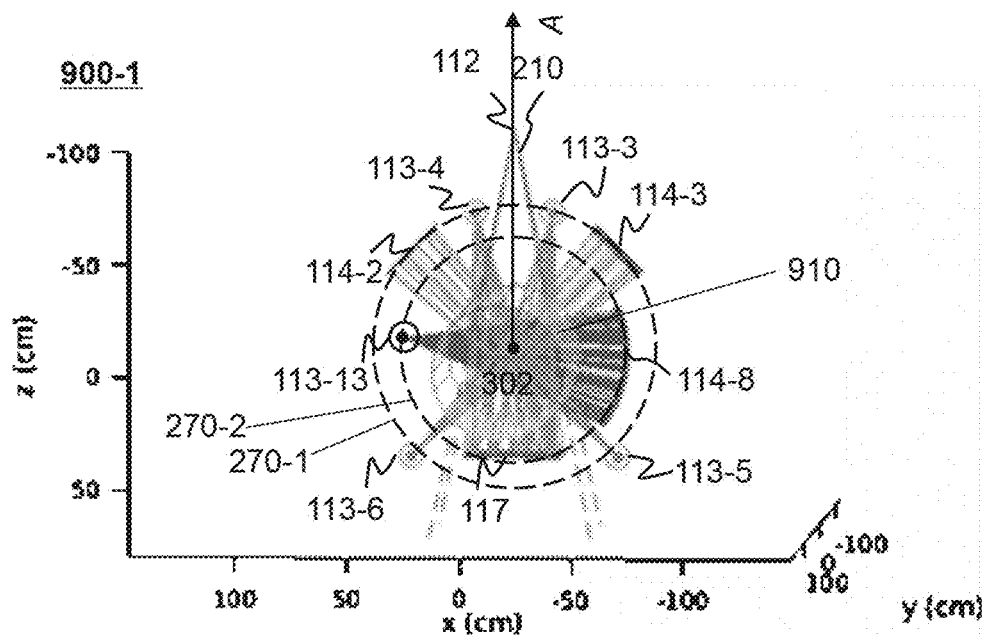

FIG. 9A is a schematic diagram illustrating an exemplary configuration 900-1 of the radiation device 110 according to some embodiments of the present disclosure. On the basis of the configuration 400 in FIG. 4, the radiation device 110 further includes an imaging radiation source 113-13 and a first detector 114-8. The imaging beam emitted from the imaging radiation source 113-13 are detected by the first detector 114-8. An angle difference between a central axis of the imaging radiation source 113-13 and a central axis of the treatment beam 210 is 82.5 degrees. In some embodiments, the imaging radiation source 113-13 and the first detector 114-8 can move independently of at least one component (e.g., the treatment head 112, the imaging radiation sources 113-3 through 113-6, the first detectors 114-2 and 114-3, or the second detector 117) of the radiation device 110. Merely by way of example, an FOV (e.g., the cylinder 901 in FIG. 9A) of the imaging radiation source 113-13 at the isocenter is 60 cm. An FOV of the imaging radiation source 113-3 and 113-4 at the isocenter is 14.3 cm.

For example, a rotation radius (e.g., 50 cm) of the imaging radiation source 113-13 and the first detector 114-8 is different from a rotation radius (e.g., 65 cm) of other imaging components (e.g., including the imaging radiation sources 113-3 through 113-6, the first detectors 114-2 and 114-3, and the second detector 117) such that they move in different rotation rings (e.g., rings 270-1 and 270-2 in FIG. 9) and the imaging radiation source 113-13 and the first detector 114-8 can move in a range of 360 degrees without colliding the other imaging components.

As another example, the second detector 117 is located to move along the rotation ring 270-2. In this case, the imaging radiation source 113-13 and the corresponding first detector 114-8 are able to move independently of the second detector 117 in a limited range less than 360 degrees. The second detector 117 may be configured to move radially away from the isocenter to allow movement of the imaging radiation source 113-13 and the corresponding first detector 114-8 in a range of 360 degrees. By the radial movement of the second detector 117, the second detector 117 may make room for independent movement of the imaging radiation source 113-13 and the corresponding first detector 114-8.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 9B:
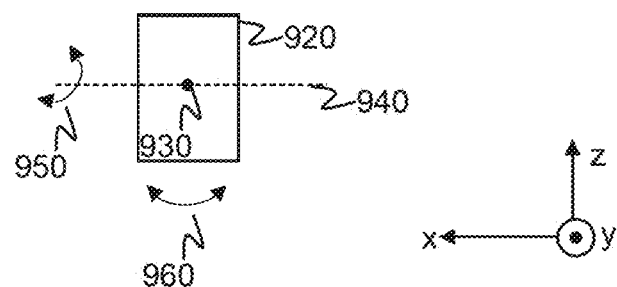
FIG. 9B is a schematic diagram illustrating an exemplary imaging radiation source according to some embodiments of the present disclosure.

FIG. 9B is a schematic diagram illustrating an exemplary imaging radiation source 920 according to some embodiments of the present disclosure. The x, y, and z directions in FIG. 9B may correspond to those in FIG. 1. In some embodiments, the imaging radiation source 920 may be configured to tilt along direction 950 with respect to a first axis (e.g., central axis 940 or an axis parallel the central axis 940) of the imaging radiation source 920 so as to adjust the direction of the imaging beam (e.g., the direction of the central axis of the imaging beam) along the y direction. In some embodiments, the imaging radiation source 920 may be configured to tilt along direction 960 with respect to a second axis (e.g., central axis 930 along the y direction or an axis parallel the central axis 930) of the imaging radiation source 920 so as to adjust the direction of the imaging beam (e.g., the direction of the central axis of the imaging beam) along the x or z direction.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, at least one of the plurality of imaging radiation sources and the corresponding first detector of the at least one imaging radiation source may be disposed associated with the back of the gantry 111 along the negative y direction in FIG. 1. As used herein, the direction from the front of the gantry 111 to the back of the gantry 111 is along the negative y direction in FIG. 1. For example, the at least one imaging radiation source and the corresponding first detector may be mounted on the back of the gantry 111, and rotate with or independently of the treatment head 112. As another example, the at least one imaging radiation source and the corresponding first detector may be disposed next to the back of the gantry 111 and rotate independently of the treatment head 112 (e.g., the gantry 111). In some embodiments, the at least one imaging radiation source and the corresponding first detector may include components of a CT device.

Merely by way of example, FIGS. 9C through 9F are schematic diagrams illustrating different exemplary configurations of a radiation device according to some embodiments of the present disclosure. The configurations 900-3 and 900-6 of the radiation device 110 shown in FIGS. 9C through 9F are side sections of the radiation device 110 viewed along the positive x direction in FIG. 1. The x, y, and z directions in FIGS. 9C through 9F may correspond to those in FIG. 1. In FIGS. 9C through 9F, the positive x direction is vertical to the paper and points inward.

Figure 9C:
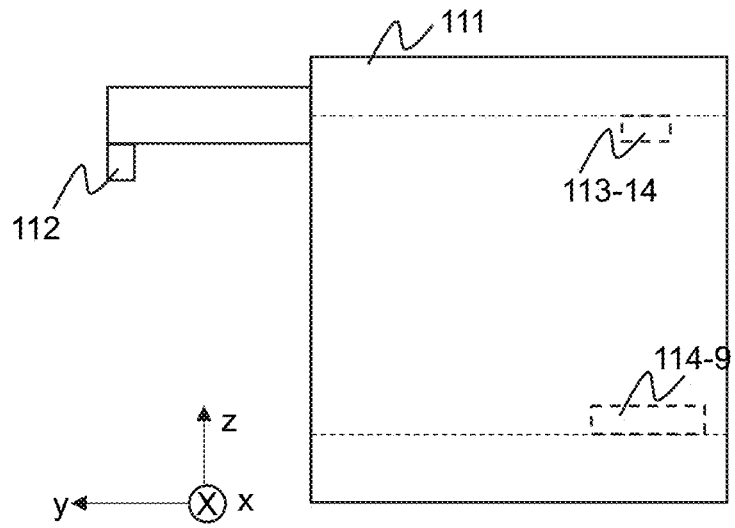
FIGS. 9C through 9F are schematic diagrams illustrating different exemplary configurations of a radiation device according to some embodiments of the present disclosure.
Figure 9D:
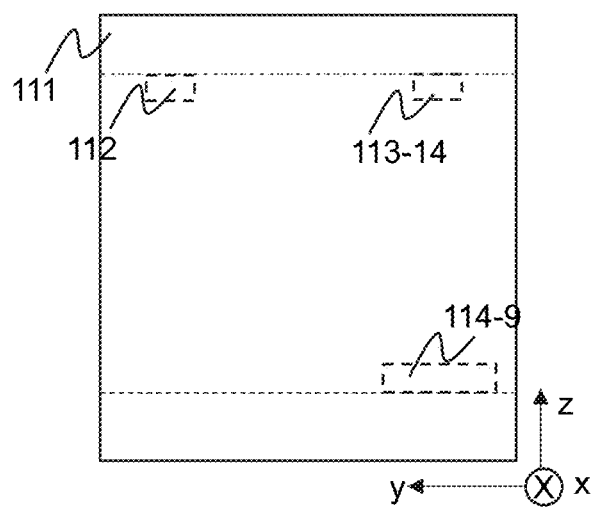

In some embodiments, as shown in FIG. 9C, the gantry 111 may include a C-arm gantry. The treatment head 112 may be mounted on the front of the C-arm gantry in a cantilever-like manner. In some embodiments, as shown in FIG. 9D, the gantry 111 may include a ring gantry having a toroidal shape. The treatment head 112 may be mounted on the front and the perimeter of the ring gantry. As shown in FIGS. 9C and 9D, the imaging radiation source 113-14 and the corresponding first detector 114-9 may be mounted on the back of the gantry 111. The imaging radiation source 113-14 and the corresponding first detector 114-9 may rotate with or independently of the treatment head 112.

Figure 9E:
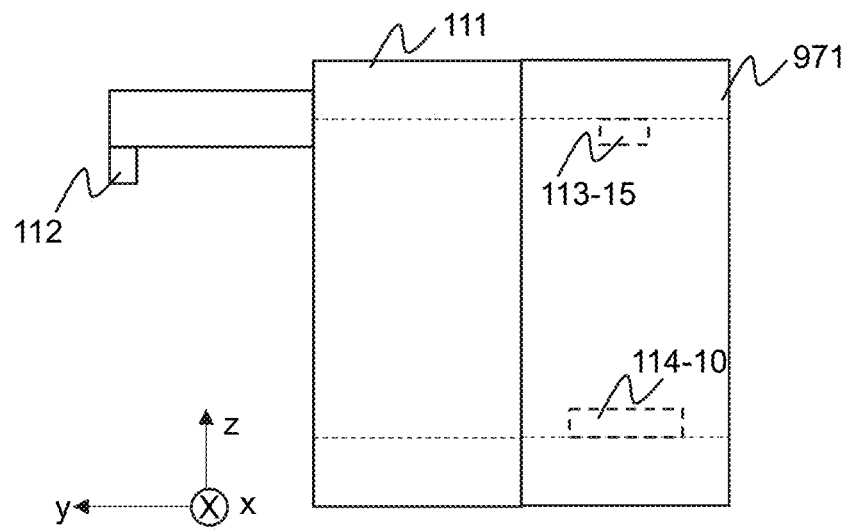
Figure 9F:
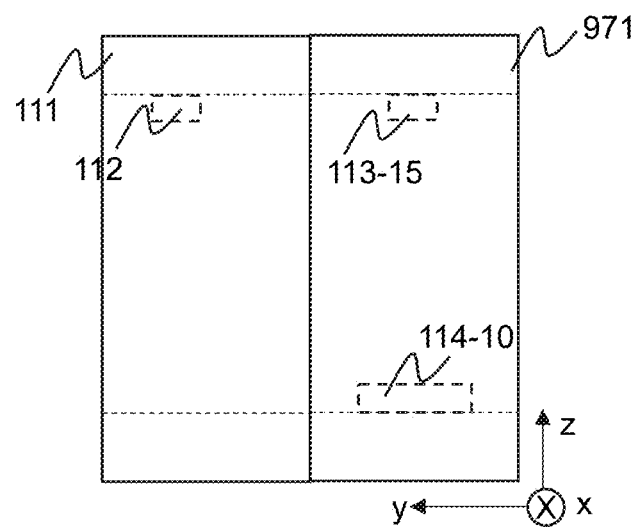

In some embodiments, as shown in FIG. 9E, the gantry 111 may include a C-arm gantry. The treatment head 112 may be mounted on the C-arm gantry in a cantilever-like manner. In some embodiments, as shown in FIG. 9F, the gantry 111 may include a ring gantry having a toroidal shape. The treatment head 112 may be mounted on the perimeter of the ring gantry. As shown in FIGS. 9E and 9F, the imaging radiation source 113-15 and the corresponding first detector 114-10 may be disposed next to the back of the gantry 111. The imaging radiation source 113-15 and the corresponding first detector 114-10 may rotate independently of the treatment head 112 (e.g., the gantry 111). For example, as shown in FIGS. 9E and 9F, the imaging radiation source 113-15 and the corresponding first detector 114-10 may be mounted on an imaging support 971 that is disposed next to the back of the gantry 111. The imaging support 971 may be in mechanical connection with or separated from the gantry 111. The imaging support 971 may rotate independently of the gantry 111.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
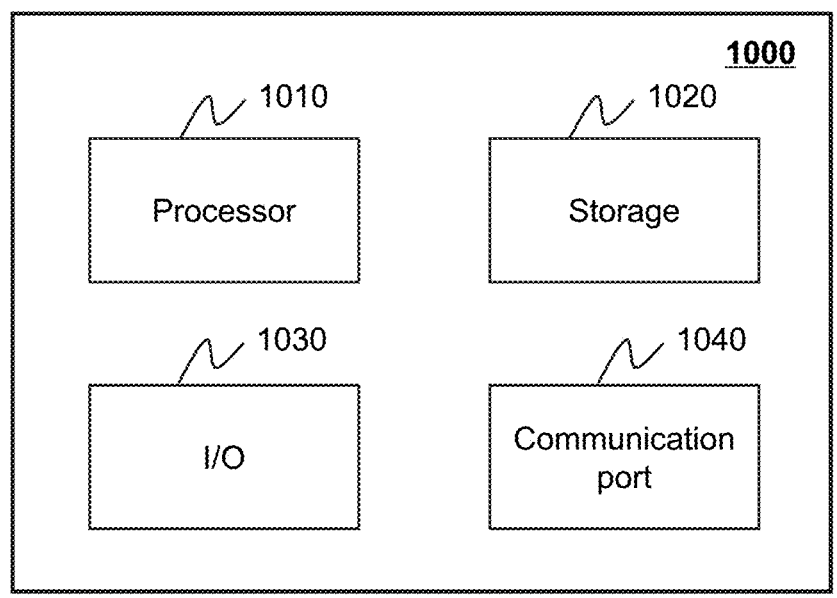
FIG. 10 is a schematic diagram illustrating exemplary hardware and/or software components of a computing device according to some embodiments of the present disclosure.

FIG. 10 is a schematic diagram illustrating exemplary hardware and/or software components of a computing device on which the processing device120 may be implemented according to some embodiments of the present disclosure. As illustrated in FIG. 10, the computing device 1000 may include a processor 1010, a storage 1020, an input/output (I/O) 1030, and a communication port 1040.

The processor 1010 may execute computer instructions (program code) and perform functions of the processing device120 in accordance with techniques described herein. The computer instructions may include routines, programs, objects, components, signals, data structures, procedures, modules, and functions, which perform particular functions described herein. For example, the processor 1010 may process data obtained from the radiation device 110, the terminal 140, the storage device 130, or any other component of the medical radiation system 100. In some embodiments, the processor 1010 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 1000. However, it should be note that the computing device 1000 in the present disclosure may also include multiple processors, thus operations and/or method steps that are performed by one processor as described in the present disclosure may also be jointly or separately performed by the multiple processors. For example, if in the present disclosure the processor of the computing device 1000 executes both step A and step B, it should be understood that step A and step B may also be performed by two different processors jointly or separately in the computing device 1000 (e.g., a first processor executes step A and a second processor executes step B, or the first and second processors jointly execute steps A and B).

The storage 1020 may store data/information obtained from the radiation device 110, the terminal 140, the storage device 130, or any other component of the medical radiation system 100. In some embodiments, the storage 1020 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 1020 may store one or more programs and/or instructions to perform exemplary methods described in the present disclosure.

The I/O 1030 may input or output signals, data, or information. In some embodiments, the I/O 1030 may enable a user interaction with the processing device 120. For example, the processing device may display an image through the I/O 1030. In some embodiments, the I/O 1030 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 1040 may be connected to a network (e.g., the network 150) to facilitate data communications. The communication port 1040 may establish connections between the processing device120 and the Radiation device 110, the terminal 140, or the storage device 130. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 1040 may be designed in accordance with the digital imaging and communications in medicine (DICOM) protocol.

Figure 11:
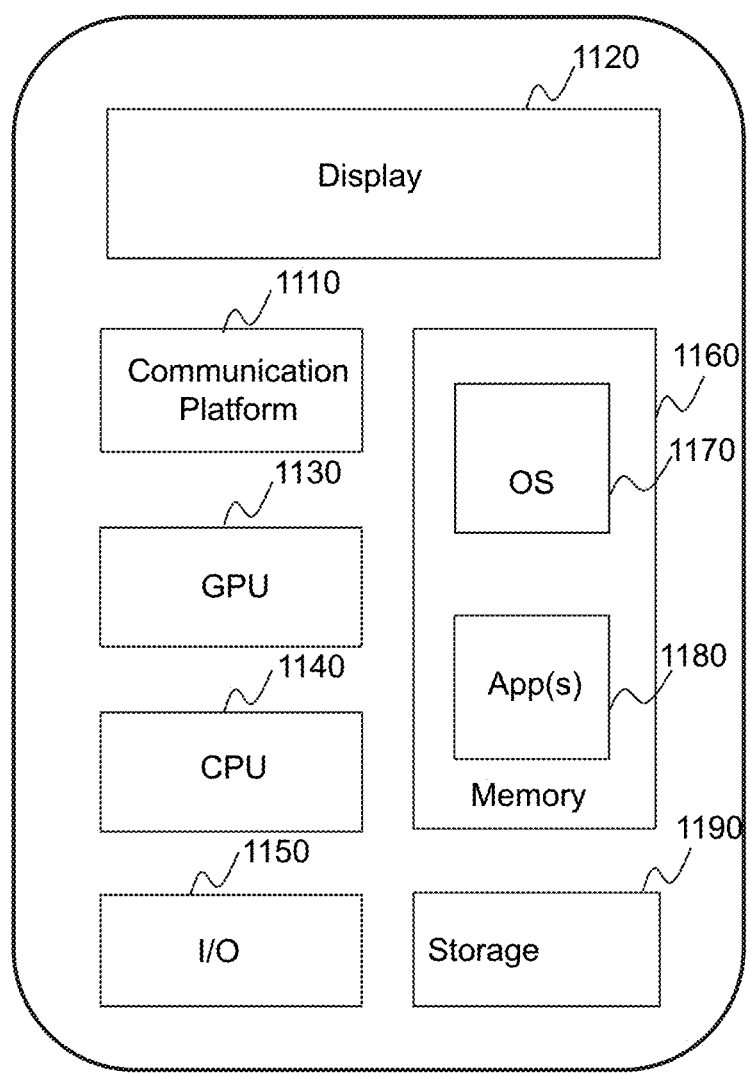
FIG. 11 is a schematic diagram illustrating exemplary hardware and/or software components of a mobile device according to some embodiments of the present disclosure.

FIG. 11 is a schematic diagram illustrating exemplary hardware and/or software components of a mobile device on which the terminal 140 may be implemented according to some embodiments of the present disclosure. As illustrated in FIG. 11, the mobile device 1100 may include a communication platform 1110, a display 1120, a graphics processing unit (GPU) 1130, a central processing unit (CPU) 1140, an I/O 1150, a memory 1160, and a storage 1190. In some embodiments, any other suitable component, including but not limited to a system bus or a controller (not shown), may also be included in the mobile device 1100. In some embodiments, a mobile operating system 1170 (e.g., iOS, Android, Windows Phone, etc.) and one or more applications 1180 may be loaded into the memory 1160 from the storage 1190 in order to be executed by the CPU 1140. The applications 1180 may include a browser or any other suitable mobile apps for receiving and rendering information relating to image processing or other information from the processing device 120. User interactions with the information stream may be achieved via the I/O 1150 and provided to the processing device 120 and/or other components of the medical radiation system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 12:
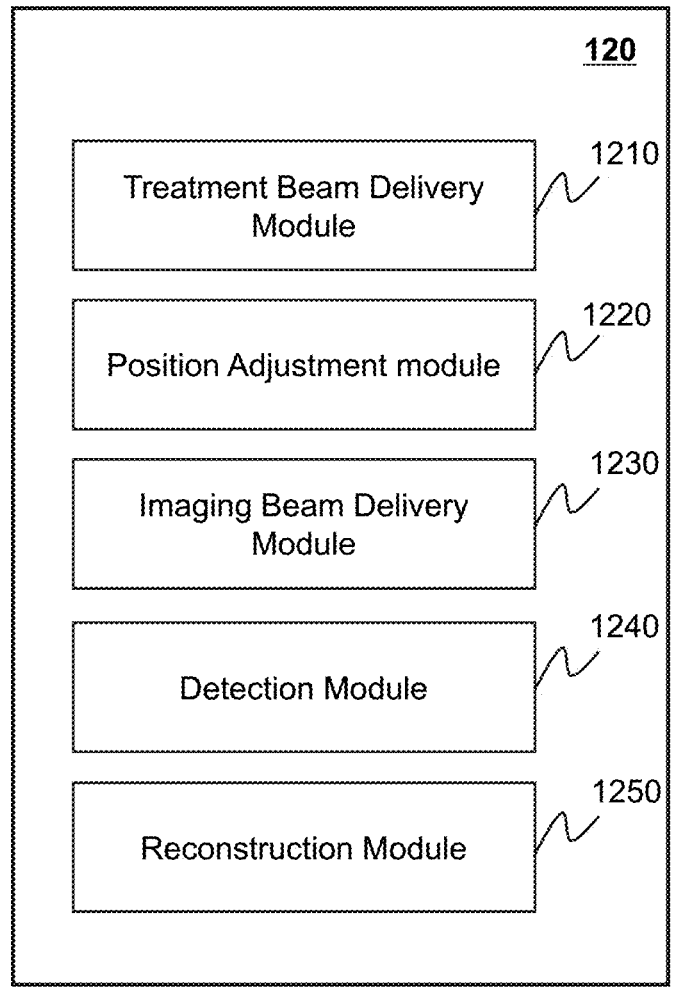
FIG. 12 is a block diagram illustrating an exemplary processing device according to some embodiments of the present disclosure.

FIG. 12 is a block diagram illustrating an exemplary processing device according to some embodiments of the present disclosure. The processing device 120 may include a treatment beam delivery module 1210, a position adjustment module 1220, an imaging beam delivery module 1230, a detection module 1240, and a reconstruction module 1250.

The treatment beam delivery module 1210 may cause the treatment head 112 to deliver the treatment beam 210 to an object. The treatment beam 210 may provide a maximum treatment radiation region.

The position adjustment module 1220 may cause a plurality of imaging radiation sources and one or more first detectors to be positioned outside at least a portion of the maximum treatment radiation region so as not to interfere with the treatment beam. In some embodiments, at least one of the plurality of imaging radiation sources and the one or more first detectors may be positioned at or near an edge of the maximum treatment radiation region. Details regarding positioning the plurality of imaging radiation sources and the one or more first detectors so as not to interfere with the treatment beam can be found elsewhere in the present disclosure (e.g., in connection with FIGS. 2-8 and 9A).

The imaging beam delivery module 1230 may cause the plurality of imaging radiation sources to deliver first imaging beams to the object while the treatment head 112 is delivering the treatment beam to the object.

The detection module 1240 may acquire a first data set generated by the one or more first detectors by detecting at least a portion of the first imaging beams.

If a first angular projection range of a combination of the plurality of static imaging radiation sources is a portion of a full angular projection range of the radiation device 110, the position adjustment module 1220 may cause the plurality of imaging radiation sources to move and deliver second imaging beams to the object so as to cover a second angular projection range. The first angular projection range and the second angular projection range may constitute the full angular projection range. In some embodiments, the position adjustment module 1220 may cause the plurality of imaging radiation sources to move and deliver the second imaging beams when the treatment beam is on or off.

The detection module 1240 may acquire a second data set generated by the one or more first detectors by detecting at least a portion of the second imaging beams.

The reconstruction module 1250 may generate an image of the object based on at least a portion of the first data set and/or the second data set. In some embodiments, the reconstruction module 1250 may reconstruct the image using a reconstruction algorithm. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

In some embodiments, the treatment beam may be detected by at least one second detector to generate a third data set (e.g., projection data). The reconstruction module 1250 may generate the image of the object based further on the third data set. In some embodiments, at least a portion of the first imaging beams may be detected by at least one second detector to generate a fourth data set (e.g., projection data). The reconstruction module 1250 may generate the image of the object based further on the fourth data set. In some embodiments, at least a portion of the second imaging beams may be detected by at least one second detector to generate a fifth data set (e.g., projection data). The reconstruction module 1250 may generate the image of the object based further on the fifth data set.

In some embodiments, the treatment beam in 1310 may be delivered to a target volume of the object to perform a radiotherapy on the target volume. In some embodiments, the position of the target volume may change with time due to various motions, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, filling/emptying of bladder, rectum and digestive system, or the like, or any combination thereof. The generated image may be used to monitor the position and/or the motion of the target volume during the radiotherapy.

In some embodiments, the treatment beam delivery module 1210 may determine, based on the images, whether any change or adjustment is needed with respect to a treatment plan of the radiotherapy. In some embodiments, when detecting a movement or change of the target volume, the treatment beam delivery module 1210 may revise the delivery of the treatment beam or the position of the object. For example, the treatment beam delivery module 1210 may pause the delivery of the treatment beam, and then adjust the treatment head to target at the position of the moved or changed target volume. As another example, the treatment beam delivery module 1210 may pause the delivery of the treatment beam, and then adjust the position of the target volume with respect to the treatment beam to make the treatment beam target at the target volume. After the delivery of the treatment beam or the position of the object is adjusted, the treatment head may resume the delivery of the treatment beam. In some embodiments, when detecting the movement or change of the target volume, the treatment head may terminate the delivery. In some embodiments, the treatment beam delivery module 1210 may generate a notification based on the detected movement or change of the target volume. In some embodiments, the notification may include information of the movement or change of the target volume. The notification may be in a form of text, video, audio, etc.

According to the systems and methods described in the present disclosure, during a radiotherapy on a target volume, the treatment beam delivery module 1210 may automatically generate and/or analyze images to record the radiotherapy, monitor the position of the target volume, assess the change of the position of the target volume, and/or determine how to proceed further with a treatment plan of the radiotherapy (e.g., to continue the radiotherapy as planned, to continue the radiotherapy with a revised plan, or to terminate the radiotherapy, etc.). In some embodiments, the monitoring, assessment, and/or adjustment may be performed semi-automatically with the input of a user (e.g., a doctor). For instance, the treatment beam delivery module 1210 may transmit the images to be presented on the terminal 130 (e.g., a display) so that the user may analyze the images and provide an instruction as to how to proceed further with the treatment plan (e.g., to continue the radiotherapy as planned, to continue the radiotherapy with a revised plan, or to terminate the radiotherapy, etc.). As another example, the treatment beam delivery module 1210 may first analyze the images and determine if any change occurs in the target volume and how much the change is. The treatment beam delivery module 1210 may determine accordingly if any adjustment in the treatment plan is needed. If the change of the target volume or the adjustment needed in the treatment plan is within a threshold, the treatment beam delivery module 1210 may adjust automatically. In some embodiments, a notification may be generated when the treatment beam delivery module 1210 makes such a determination. If the change of the target volume or the adjustment needed in the treatment plan is not within a threshold, the treatment beam delivery module 1210 may generate a notification to, e.g., the user to seek instructions from the user as to how to proceed further.

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module (not shown in FIG. 12). The storage module may be configured to store data generated during any process performed by any component of in the processing device 120. As another example, each of components of the processing device 120 may include a storage apparatus. Additionally or alternatively, the components of the processing device 120 may share a common storage apparatus.

Figure 13:
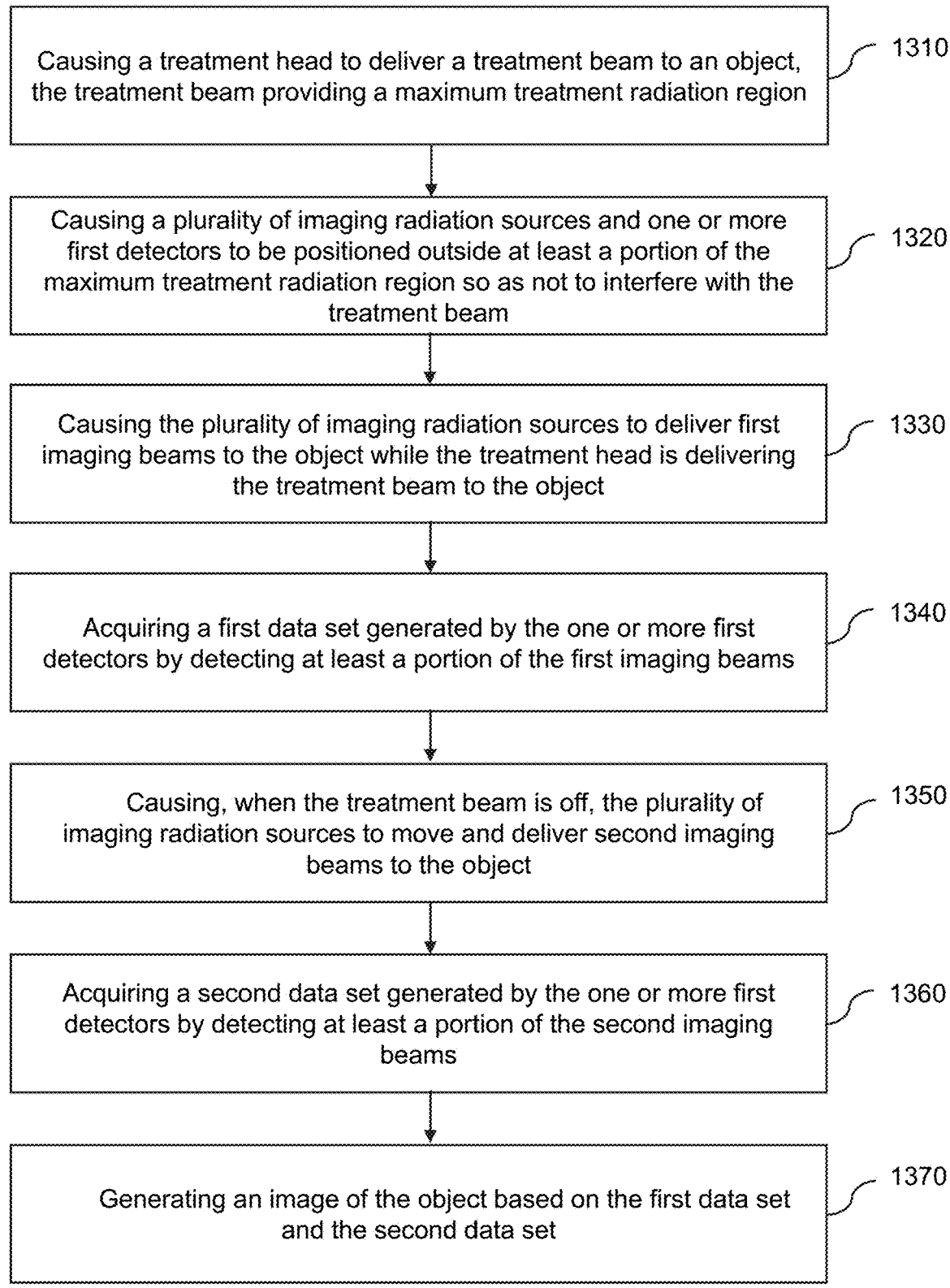
FIG. 13 is a flowchart illustrating an exemplary imaging process f according to some embodiments of the present disclosure.

FIG. 13 is a flowchart illustrating an exemplary imaging process according to some embodiments of the present disclosure. The process 1300 may be implemented in the medical radiation system 100 illustrated in FIG. 1. For example, the process 1300 may be stored in the storage device 130 and/or the storage 1020 in the form of instructions (e.g., an application), and invoked and/or executed by the processing device 120 (e.g., the processor 1010 illustrated in FIG. 10, or one or more modules in the processing device 120 illustrated in FIG. 12). The operations of the illustrated process presented below are intended to be illustrative. In some embodiments, the process 1300 may be accomplished with one or more additional operations not described, and/or without one or more of the operations discussed. Additionally, the order in which the operations of the process 1300 as illustrated in FIG. 13 and described below is not intended to be limiting.

In 1310, the processing device 120 (e.g., the treatment beam delivery module 1210) may cause the treatment head 112 to deliver the treatment beam 210 to an object. The treatment beam 210 may provide a maximum treatment radiation region.

In 1320, the processing device 120 (e.g., the position adjustment module 1220) may cause a plurality of imaging radiation sources and one or more first detectors to be positioned outside at least a portion of the maximum treatment radiation region so as not to interfere with the treatment beam. In some embodiments, at least one of the plurality of imaging radiation sources and the one or more first detectors may be positioned at or near an edge of the maximum treatment radiation region. Details regarding positioning the plurality of imaging radiation sources and the one or more first detectors so as not to interfere with the treatment beam can be found elsewhere in the present disclosure (e.g., in connection with FIGS. 2 through 8 and 9A).

In 1330, the processing device 120 (e.g., the imaging beam delivery module 1230) may cause the plurality of imaging radiation sources to deliver first imaging beams to the object while the treatment head 112 is delivering the treatment beam to the object.

In 1340, the one or more first detectors may detect at least a portion of the first imaging beams. The processing device 120 may acquire a first data set (e.g., projection data) based on the detected first imaging beams.

In 1350, if a first angular projection range of a combination of the plurality of static imaging radiation sources is a portion of a full angular projection range of the radiation device 110, the processing device 120 (e.g., the position adjustment module 1220) may cause the plurality of imaging radiation sources to move and deliver second imaging beams to the object so as to cover a second angular projection range. The first angular projection range and the second angular projection range may constitute the full angular projection range. In some embodiments, the processing device 120 may cause the plurality of imaging radiation sources to move and deliver the second imaging beams when the treatment beam is on or off.

In 1360, the one or more first detectors to detect at least a portion of the second imaging beams. The processing device 120 may acquire a second data set (e.g., projection data) based on the detected second imaging beams.

In 1370, the processing device 120 (e.g., the reconstruction module 1250) may generate an image of the object based on at least a portion of the first data set and/or the second data set. In some embodiments, the processing device 120 may reconstruct the image using a reconstruction algorithm. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

In some embodiments, the treatment beam may be detected by at least one second detector to generate a third data set (e.g., projection data). The processing device 120 may generate the image of the object based further on the third data set. In some embodiments, at least a portion of the first imaging beams may be detected by at least one second detector to generate a fourth data set (e.g., projection data). The processing device 120 may generate the image of the object based further on the fourth data set. In some embodiments, at least a portion of the second imaging beams may be detected by at least one second detector to generate a fifth data set (e.g., projection data). The processing device 120 may generate the image of the object based further on the fifth data set.

In some embodiments, the treatment beam in 1310 may be delivered to a target volume of the object to perform a radiotherapy on the target volume. In some embodiments, the position of the target volume may change with time due to various motions, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, filling/emptying of bladder, rectum and digestive system, or the like, or any combination thereof. The image generated in 1270 may be used to monitor the position and/or the motion of the target volume during the radiotherapy.

In some embodiments, the processing device 120 may determine, based on the images, whether any change or adjustment is needed with respect to a treatment plan of the radiotherapy. In some embodiments, when detecting a movement or change of the target volume, the processing device 120 may revise the delivery of the treatment beam or the position of the object. For example, the processing device 120 may pause the delivery of the treatment beam, and then adjust the treatment head to target at the position of the moved or changed target volume. As another example, the processing device 120 may pause the delivery of the treatment beam, and then adjust the position of the target volume with respect to the treatment beam to make the treatment beam target at the target volume. After the delivery of the treatment beam or the position of the object is adjusted, the treatment head may resume the delivery of the treatment beam. In some embodiments, when detecting the movement or change of the target volume, the treatment head may terminate the delivery. In some embodiments, the processing device 120 may generate a notification based on the detected movement or change of the target volume. In some embodiments, the notification may include information of the movement or change of the target volume. The notification may be in a form of text, video, audio, etc.

According to the systems and methods described in the present disclosure, during a radiotherapy on a target volume, the processing device 120 may automatically generate and/or analyze images to record the radiotherapy, monitor the position of the target volume, assess the change of the position of the target volume, and/or determine how to proceed further with a treatment plan of the radiotherapy (e.g., to continue the radiotherapy as planned, to continue the radiotherapy with a revised plan, or to terminate the radiotherapy, etc.). In some embodiments, the monitoring, assessment, and/or adjustment may be performed semi-automatically with the input of a user (e.g., a doctor). For instance, the processing device 120 may transmit the images to be presented on the terminal 130 (e.g., a display) so that the user may analyze the images and provide an instruction as to how to proceed further with the treatment plan (e.g., to continue the radiotherapy as planned, to continue the radiotherapy with a revised plan, or to terminate the radiotherapy, etc.). As another example, the processing device 120 may first analyze the images and determine if any change occurs in the target volume and how much the change is. The processing device 120 may determine accordingly if any adjustment in the treatment plan is needed. If the change of the target volume or the adjustment needed in the treatment plan is within a threshold, the processing device 120 may adjust automatically. In some embodiments, a notification may be generated when the processing device 120 makes such a determination. If the change of the target volume or the adjustment needed in the treatment plan is not within a threshold, the processing device 120 may generate a notification to, e.g., the user to seek instructions from the user as to how to proceed further.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation treatment system comprising:
    a gantry configured to rotate around an object;
    a treatment head moving with the gantry, the treatment head being configured to deliver a treatment beam to the object, the treatment beam providing a maximum treatment radiation region;
    a plurality of imaging radiation sources configured to emit imaging beams toward the object; and
    one or more first detectors configured to detect at least a portion of the imaging beams, wherein when the treatment head is delivering the treatment beam to the object, the plurality of imaging radiation sources and the one or more first detectors are positioned outside at least a portion of the maximum treatment radiation region so as not to interfere with the treatment beam, at least one of the plurality of imaging radiation sources being positioned at an edge of the maximum treatment radiation region,
    wherein when the treatment head is delivering the treatment beam to the object along a first direction, the first direction being along a central axis of the treatment beam emitted from the treatment head and distal to the treatment head, the at least one of the plurality of imaging radiation sources is positioned so that the at least one of the plurality of imaging radiation sources delivers an imaging beam along a second direction, the second direction being along a central axis of the imaging beam emitted from the at least one of the plurality of imaging radiation sources and distal to the at least one of the plurality of imaging radiation sources, a difference between the first direction and the second direction is less than 30 degrees.

2. The system of claim 1, wherein
    the treatment beam provides a maximum treatment field on an isocenter plane of the treatment beam;
    the treatment beam is collimated to a target-specific treatment area that is smaller than the maximum treatment field, and
    at least one imaging radiation source is positioned such that a projection of the at least one imaging radiation source onto the isocenter plane is within the maximum treatment field.

3. The system of claim 1, wherein at least one of the plurality of imaging radiation sources or the one or more first detectors is configured to move independently of the gantry.

4. The system of claim 3, wherein the at least one of the plurality of imaging radiation sources or the one or more first detectors is mounted on a ring other than the gantry.

5. The system of claim 1, wherein at least one first imaging radiation source of the plurality imaging radiation sources is configured to move, along with the corresponding first detector, around a rotation axis of the gantry and independently of the gantry in a first range without collision with other components of the radiation device.

6. The system of claim 1, wherein at least one of the plurality of imaging radiation sources is configured to rotationally oscillate in a limited angle range less than 360 degrees.

7. The system of claim 1, further comprising:
    a second detector located opposite to the treatment head and configured to detect the treatment beam.

8. The system of claim 7, wherein the second detector is configured to detect an imaging beam emitted from at least one of the plurality of imaging radiation sources.

9. The system of claim 1, wherein at least one second imaging radiation source of the plurality of imaging radiation sources is rotatable and located on a plane different from the rotation plane of the treatment head.

10. The system of claim 9, wherein a rotation plane of each of the at least one second imaging radiation source is perpendicular to the rotation plane of the treatment head.

11. The system of claim 1, wherein at least a portion of the detected imaging beams are transformed into three-dimensional (3D) projection data to reconstruct a 3D imaging of the object.

12. The system of claim 1, wherein at least one of the plurality of imaging radiation sources and the corresponding first detector of the at least one imaging radiation source are mounted on the back of the gantry along a rotation axis of the gantry, the back of the gantry being on a side of the gantry from which the object is moved out of the radiation treatment system.

13. The system of claim 1, wherein when the treatment head is delivering the treatment beam to the object, the plurality of imaging radiation sources are positioned on a first side of the maximum treatment radiation region, and the one or more first detectors are positioned on a second side of the maximum treatment radiation region.

14. The system of claim 1, wherein the one or more first detectors and the plurality of imaging radiation sources are alternately arranged.

15. The system of claim 1, wherein rotation radiuses of at least two of the plurality of imaging radiation sources are different.

16. The system of claim 1, wherein
    a first angular projection range of the plurality of imaging radiation sources is a portion of a full angular projection range of the radiation treatment system;
    the plurality of imaging radiation sources are further configured to rotationally oscillate to cover a second angular projection range, the first angular projection range and the second angular projection range constituting the full angular projection range of the radiation treatment system; and
    a rotation radius of the plurality of first imaging radiation resources is different from a rotation radius of the treatment head.

17. The system of claim 1, wherein the full angular projection range is a sum of at least 180 degrees and an imaging beam cone angle.

18. An imaging method implemented on a machine having one or more processors and one or more storage devices, the method comprising:
    causing a treatment head of a radiation treatment system to deliver, according to a treatment plan, a treatment beam to an object, the treatment beam providing a maximum treatment radiation region;

causing a plurality of imaging radiation sources and one or more first detectors of the radiation treatment system to be positioned outside the maximum treatment radiation region so as not to interfere with the treatment beam, at least one of the plurality of imaging radiation sources being positioned at an edge of the maximum treatment radiation region, wherein when the treatment head is delivering the treatment beam to the object along a first direction, the first direction being along a central axis of the treatment beam emitted from the treatment head and distal to the treatment head, the at least one of the plurality of imaging radiation sources is positioned so that the at least one of the plurality of imaging radiation sources delivers an imaging beam along a second direction, the second direction being along a central axis of the imaging beam emitted from the at least one of the plurality of imaging radiation sources and distal to the at least one of the plurality of imaging radiation sources, a difference between the first direction and the second direction is less than 30 degrees;

causing the plurality of imaging radiation sources to deliver first imaging beams to the object while the treatment head is delivering the treatment beam to the object;

acquiring a first data set generated by the one or more first detectors by detecting at least a portion of the first imaging beams; and generating an image of the object based on the first data set.

19. An imaging system, comprising:

at least one storage device including a set of instructions;

at least one processor in communication with the at least one storage device, wherein when executing the set of instructions, the at least one processor is configured to cause the system to perform operations including:

causing a treatment head of a radiation treatment system to deliver, according to a treatment plan, a treatment beam to an object, the treatment beam providing a maximum treatment radiation region;

causing a plurality of imaging radiation sources and one or more first detectors of the radiation treatment system to be positioned outside the maximum treatment radiation region so as not to interfere with the treatment beam, at least one of the plurality of imaging radiation sources being positioned at an edge of the maximum treatment radiation region, wherein when the treatment head is delivering the treatment beam to the object along a first direction, the first direction being along a central axis of the treatment beam emitted from the treatment head and distal to the treatment head, the at least one of the plurality of imaging radiation sources is positioned so that the at least one of the plurality of imaging radiation sources delivers an imaging beam along a second direction, the second direction being along a central axis of the imaging beam emitted from the at least one of the plurality of imaging radiation sources and distal to the at least one of the plurality of imaging radiation sources, a difference between the first direction and the second direction is less than 30 degrees;

causing the plurality of imaging radiation sources to deliver first imaging beams to the object while the treatment head is delivering the treatment beam to the object;

acquiring a first data set generated by the one or more first detectors by detecting at least a portion of the first imaging beams; and generating an image of the object based on the first data set.

20. The system of claim 19, wherein the at least one processor is configured to cause the system to perform the operations including:

adjusting the treatment plan based on the image; and causing, according to the adjusted treatment plan, the treatment head to deliver an adjusted treatment beam to the object or to pause the delivery of the treatment beam.

* * * * *